(12) United States Patent
Liu et al.

(10) Patent No.: US 8,389,264 B2
(45) Date of Patent: Mar. 5, 2013

(54) **RECOMBINANT MICROORGANISM THAT EXPRESSES A *SECY* GENE WITH DELETION OF SPORULATION-ASSOCIATED GENES AND METHOD OF PRODUCING THEREOF**

(75) Inventors: Shenghao Liu, Haga-gun (JP); Keiji Endo, Haga-gun (JP); Katsutoshi Ara, Haga-gun (JP)

(73) Assignee: Kao Corporation, Tokyo (JP)

( * ) Notice: Subject to any disclaimer, the term of this patent is extended or adjusted under 35 U.S.C. 154(b) by 156 days.

(21) Appl. No.: 12/530,135

(22) PCT Filed: Apr. 8, 2008

(86) PCT No.: PCT/JP2008/057229
§ 371 (c)(1),
(2), (4) Date: Sep. 4, 2009

(87) PCT Pub. No.: WO2008/126929
PCT Pub. Date: Oct. 23, 2008

(65) Prior Publication Data
US 2011/0151567 A1 Jun. 23, 2011

(30) Foreign Application Priority Data
Apr. 10, 2007 (JP) ................................. 2007-102940

(51) Int. Cl.
*C12N 1/21* (2006.01)
(52) U.S. Cl. ............ 435/252.3; 435/252.31; 435/254.11; 435/209; 435/69.1
(58) Field of Classification Search ............... 435/252.3, 435/252.31, 254.11, 209, 69.1
See application file for complete search history.

(56) References Cited

U.S. PATENT DOCUMENTS

| | | | |
|---|---|---|---|
| 3,844,890 A | 10/1974 | Horikoshi et al. | |
| 4,945,053 A | 7/1990 | Ito et al. | |
| 5,726,042 A * | 3/1998 | Shivakumar et al. | ........ 435/69.1 |
| 7,585,674 B2 | 9/2009 | Sawada et al. | |
| 2003/0157642 A1 * | 8/2003 | Caldwell et al. | ............. 435/69.1 |
| 2004/0248279 A1 * | 12/2004 | Sawada et al. | ........... 435/252.31 |
| 2006/0057674 A1 | 3/2006 | Hintz et al. | |
| 2009/0029417 A1 | 1/2009 | Endo et al. | |

FOREIGN PATENT DOCUMENTS

| | | | |
|---|---|---|---|
| EP | 492274 A2 * | 7/1992 | |
| GB | 2095275 A | 9/1982 | |
| JP | 50-28515 B | 9/1975 | |
| JP | 60-23158 B | 6/1985 | |
| JP | 4-190793 A | 7/1992 | |
| JP | 6-030578 B2 | 4/1994 | |
| JP | 2000-210081 A | 8/2000 | |
| JP | 2001-510046 A | 7/2001 | |
| JP | 2003-47490 A | 2/2003 | |
| JP | 2004-173598 | * | 6/2004 |
| JP | 2004173598 A | * | 6/2004 |
| JP | 2005-137308 A1 | 6/2005 | |
| JP | 2006-296268 A1 | 11/2006 | |
| JP | 2007-049987 A1 | 3/2007 | |
| WO | WO 99/04006 A1 | 1/1999 | |
| WO | WO 03/066818 A2 | 8/2003 | |
| WO | WO 2004/060909 A2 | 7/2004 | |
| WO | WO 2007/094136 A1 | 8/2007 | |

OTHER PUBLICATIONS

Witkowski et al. Conversion of a beta-Ketoacyl Synthase to a Malonyl Decarboxylase by Replacement of the Active-Site Cysteine with Glutamine; Biochemistry 38:11643-11650, 1999.*
Seffernick et al.; Melamine Deaminase and Atrazine Chlorohydrolase: 98 Percent Identical but Functionally Different; J. Bacteriol. 183(8):2405-2410, 2001.*
Zuber et al.; Mutation Changing the Specificity of an RNA Polymerase Sigma Factor; Journal of Molecular Biology 206: 605-614 (1989).*
Branden et al. (Introduction to Protein Structure, Garland Publishing Inc., New York, p. 247; 1991).*
Attwood, T. K.; The Babel of Bioinformatics; Science vol. 290, 471-473; Oct. 20, 2000.*
Merriam-Webster "as well as" definition; accessed on-line Aug. 6, 2012.*
Blattner, F. R., et al., "The Complete Genome Sequence of *Escherichia coli* K-12," *Science* 277:1453-1462, American Association for the Advancement of Science, Washington, DC (1997).
Brigidi, P. et al., "Genetic transformation of intact cells of *Bacillus subtilis* by electroporation," *FEMS Microbiology Letters* 67:135-138, Elsevier Science Publishers, B.V., Amsterdam, The Netherlands (1990).
Burbulys, D. et al., "Initiation of Sporulation in *B. subtilis* is Controlled by a Multicomponent Phosphorelay," *Cell* 64(3):545-52, Cell Press, Cambridge, Massachusetts, USA (1991).
Chang, S et al., "High Frequency Transformation of *Bacillus subtilis* Protoplasts by Plasmid DNA," *Molecular & General Genetics* 168(1):111-115, Springer-Verlag, Berlin, Germany (1979).
Coppolecchia, R. et al.,"Deletion of *spoIIAB* Blocks Endospore Formation in *Bacillus subtilis* at an Early Stage," *J. Bacteriol.* 173(21):6678-6685, American Society for Microbiology, Washington, DC, USA (1991).

(Continued)

*Primary Examiner* — Michele K Joike
*Assistant Examiner* — Antonio Galisteo Gonzalez
(74) *Attorney, Agent, or Firm* — Sterne, Kessler, Goldstein & Fox P.L.L.C.

(57) ABSTRACT

A recombinant microorganism having improved productivity for a protein or a polypeptide, and a method for producing a protein or a polypeptide using the recombinant microorganism, are provided.

A recombinant microorganism obtained by transfecting a gene for encoding a desired protein or polypeptide into a microorganism strain which is obtained by genetically constructing to overexpress secY gene of *Bacillus subtilis* or a gene corresponding to the secY gene, and deleting or inactivating one or more genes selected from sporulation-associated genes and genes corresponding to the sporulation-associated genes from the genome.

11 Claims, 4 Drawing Sheets

OTHER PUBLICATIONS

Hellman, J. and Moran, C., "RNA Polymerase and Sigma Factors" in "*Bacillus subtilis* and Its Closest Relatives: From Genes to Cells", A.L. Sonenshein et al., eds., pp. 289-312, ASM Press, Washington, DC (2002).

Henrissat B., "A classification of glycosyl hydrolases based on amino acid sequence similarities," *Biochemistry J.* 280:309-316, Portland Press Ltd., UK (1991).

Hoch, J.A. et al., "Transformation and Transduction in Recombination-defective Mutants of *Bacillus subtilis*," *J. Bacteriol.* 93(6):1925-1937, American Society for Microbiology, Washington, DC, USA (1967).

Horinouchi, S. et al., "Nucleotide Sequence and Functional Map of pC194, a Plasmid that Specifies Inducible Chloramphenicol Resistance," *J. Bacteriol.* 150(2):815-825, American Society for Microbiology, Washington, DC, USA (1982).

Huang, X., et al., "The *Bacillus subtilis* $\sigma^x$ Protein is an Extracytoplasmic Function σ Factor Contributing to Survival at High Temperature," *J. Bacteriol.* 179:2915-2921, American Society for Microbiology, Washington, DC, USA (1997).

Horton, R.M. et al., "Engineering hybrid genes without the use of restriction enzymes: gene splicing by overlap extension," *Gene* 77: 61-68, Elsevier, Science Publishers, B.V., Amsterdam, The Netherlands (1989).

Itaya, M. et al., "Gene-directed mutagenesis on the chromosome of *Bacillus subtilis* 168," *Molecular & General Genetics* 223(2):268-272, Springer-Verlag, Berlin, Germany (1990).

Ito, K. et al., "A Temperature-Sensitive Mutant of *E. coli* Exhibiting Slow Processing of Exported Proteins," *Cell* 32:789-797, The MIT Press, Cambridge, Massachusetts, USA (1983).

Karow, M. et al., "Identification of a gene, *spoIIR*, that links the activation of $\sigma^E$ to the transcriptional activity of $\sigma^F$ during sporulation in *Bacillus subtilis*," *Proc. Nat.l Acad. Sci.* 92:2012-2016, The National Academy of Sciences, USA (1995).

Kenney, T. et al., "Organization and Regulation of an Operon That Encodes a Sporulation-Essential Sigma Factor in *Bacillus subtilis*," *J. Bacteriol.* 169(7):3329-3339, American Society for Microbiology, Washington, DC, USA (1987).

Kobayashi, T. et al., "Purification and properties of an alkaline protease from alkalophilic *Bacillus* sp. KSM-K16," *Appl. Microbiol. Biotechnol.* 43:473-481, Springer-Verlag, Berlin, Germany (1995).

Kroos, L. et al., "Control of σ factor activity during *Bacillus subtilis* sporulation," *Molecular Microbiology* 31(5):1285-1294, Blackwell Science Ltd., UK (1999).

Kunst, F. et al., "The complete genome sequence of the gram-positive bacterium *Bacillus subtilis*," *Nature* 390:249-256, Nature Publishing Group, London, UK (1997).

Lewis, P.J. et al.,"Compartmentalized distribution of the proteins controlling the prespore-specific transcription factor $\sigma^F$ of *Bacillus subtilis*," *Genes to Cells* 1(10):881-894, Blackwell Science Ltd., UK (1996).

Lipman, D.L. and W.R. Pearson, "Rapid and Sensitive Protein Similarity Searches," *Science* 227:1435-1441, American Association for the Advancement of Science, Washington, DC (1985).

Perego, M., "A peptide export-import control circuit modulating bacterial development regulates protein phosphatases of the phosphorelay," *Proc. Natl. Acad. Sci.* 94:8612-8617, The National Academy of Sciences, USA (1997).

Quisel, J. et al., "Control of Sporulation Gene Expression in *Bacillus subtilis* by the Chromosome Partitioning Proteins Soj (ParA) and Spo0J (ParB)," *J. Bacteriol.* 182(12):3446-3451, American Society for Microbiology, Washington, DC, USA (2000).

Schmidt, R. et al., "Control of developmental transcription factor $\sigma^F$ by sporulation regulatory proteins SpoIIAA and SpoIIAB in *Bacillus subtilis*," *Proc. Natl. Acad. Sci.* 87:9221-9225, The National Academy of Sciences, USA (1990).

Shine, J. et al., "The 3'-Terminal Sequence of *Escherichia coli* 16S Ribosomal RNA: Complementarity to Nonsense Triplets and Ribosome Binding Sites," *Proc. Natl. Acad. Sci.* 71:1342-1346, The National Academy of Sciences, USA (1974).

Weir, J. et al., "Regulation of spoOH, a Gene Coding for the *Bacillus subtilis* $\sigma^H$ Factor," *J. Bacteriol.* 173(2):521-529, American Society for Microbiology, Washington, DC, USA (1991).

Esp@cenet Database, English language abstract of JP 2000-210081 A.

Esp@cenet Database, English language abstract of JP 2001-510046.

Patent Abstracts of Japan, English language abstract of JP 2003-047490 A.

International Search Report for PCT/JP2008/057229, mailed Aug. 11, 2008, European Patent Office, The Netherlands.

STN database accession No. 147:270215, English abstract of WO 2007/094136 A1, Kao Corporation, published Aug. 23, 2007.

Guérout-Fleury, A.-M. et al., "Plasmids for ectopic integration in *Bacillus subtilis*," Gene 180: 57-61 (1996), Elsevier Science B.V., The Netherlands.

Hagihara, H. et al., "Novel α-Amylase That is Highly Resistant to Chelating Reagents and Chemical Oxidants from the Alkaliphilic *Bacillus* Isolate KSM-K38," *Appl. Envir. Micrbiol.* 67: 1744-1750 (Apr. 2001), Am. Soc. Microbiology, Washington, DC.

Hudspeth, D.S.S., and Vary, P.S., "*spoVG* sequence of *Bacillus megaterium* and *Bacillus subtilis*," *Biochim. Biophys. Acta* 1130:229-231 (1992), plus Erratum published at *Biochim. Biophys. Acta* 1131:353 (1992), and Corrigendum published at *Biochim. Biophys. Acta* 1216: 509 (1993), Elsevier Publishing Company.

Zuber, P., and Losick, R., "Role of AbrB and Spo0A- and Spo0B-Dependent Utilization of a Sporulation Promoter in *Bacillus subtilis*," *J. Bacteriol.* 169:2223-2230, American Society for Microbiology (1987).

Dialog File No. 351, Accession No. 535803, Derwent World Patent Index English language abstract and patent family for JP 50-28515 B (JP1975028515 B), published Sep. 16, 1975.

Dialog File No. 351, Accession No. 2497789, Derwent World Patent Index English language abstract and patent family for JP 60-23158 B (JP1985023158 B), published Jun. 6, 1985.

Dialog File No. 351, Accession No. 6043451, Derwent World Patents Index English language abstract and patent family for JP 4-190793 (JP-A-1992-190793), published Jul. 9, 1992.

Dialog File No. 351, Accession No. 4385807, Derwent World Patents Index English language abstract and patent family for JP 6-030578 B2 (JP-B-1994-030578), published Apr. 27, 1994.

Office action for JP Patent Appl. No. 2007-102940, mailed May 8, 2012 from the Japanese Patent Office, Tokyo, Japan.

Office actions and replies from the file history of U.S. Appl. No. 12/279,271, as of Mar. 20, 2012.

* cited by examiner

SEQUENCE LISTING

<160> NUMBER OF SEQ ID NOS: 85

<210> SEQ ID NO 1

```
<211> LENGTH: 1296
<212> TYPE: DNA
<213> ORGANISM: Bacillus subtilis
<220> FEATURE:
<221> NAME/KEY: CDS
<222> LOCATION: (1)..(1296)

<400> SEQUENCE: 1 ttg ttt aaa aca atc tcc aac ttt atg cgt gtg agt gat atc agg aat      48
Met Phe Lys Thr Ile Ser Asn Phe Met Arg Val Ser Asp Ile Arg Asn
1               5                   10                  15 aaa atc ata ttc act tta ctc atg ctt atc gtc ttt cgc ata ggt gcg      96
Lys Ile Ile Phe Thr Leu Leu Met Leu Ile Val Phe Arg Ile Gly Ala
            20                  25                  30 ttt att cct gtg cct tac gtt aac gct gaa gcg tta cag gca cag tct     144
Phe Ile Pro Val Pro Tyr Val Asn Ala Glu Ala Leu Gln Ala Gln Ser
        35                  40                  45 caa atg ggt gtt ttt gat ctc ctt aat aca ttt ggc ggc ggt gcg ctt     192
Gln Met Gly Val Phe Asp Leu Leu Asn Thr Phe Gly Gly Gly Ala Leu
    50                  55                  60 tac caa ttt tcc att ttc gca atg gga att act cct tat atc acg gct     240
Tyr Gln Phe Ser Ile Phe Ala Met Gly Ile Thr Pro Tyr Ile Thr Ala
65                  70                  75                  80 tcg atc atc att cag ctg ctt cag atg gat gtg gta ccg aag ttt acc     288
Ser Ile Ile Ile Gln Leu Leu Gln Met Asp Val Val Pro Lys Phe Thr
                85                  90                  95 gag tgg tct aag caa ggt gaa gtt ggc cgc cgt aaa tta gct cag ttc     336
Glu Trp Ser Lys Gln Gly Glu Val Gly Arg Arg Lys Leu Ala Gln Phe
            100                 105                 110 aca agg tac ttt acg att gtg ctt ggt ttc atc caa gcg tta ggt atg     384
Thr Arg Tyr Phe Thr Ile Val Leu Gly Phe Ile Gln Ala Leu Gly Met
        115                 120                 125 tca tat gga ttc aac aat ctg gca aac ggt atg ctg atc gaa aaa tcc     432
Ser Tyr Gly Phe Asn Asn Leu Ala Asn Gly Met Leu Ile Glu Lys Ser
    130                 135                 140 ggt gta tcg aca tat ctt atc att gct tta gtg ctc act ggc gga act     480
Gly Val Ser Thr Tyr Leu Ile Ile Ala Leu Val Leu Thr Gly Gly Thr
145                 150                 155                 160 gcc ttt tta atg tgg ctt ggg gaa caa att act tct cat gga gta ggc     528
Ala Phe Leu Met Trp Leu Gly Glu Gln Ile Thr Ser His Gly Val Gly
                165                 170                 175 aac gga ata tcg atc att atc ttc gcg ggg att gtg tct agt att cca     576
Asn Gly Ile Ser Ile Ile Ile Phe Ala Gly Ile Val Ser Ser Ile Pro
            180                 185                 190 aaa aca att ggg caa ata tat gag act caa ttt gtc ggc agc aac gat     624
Lys Thr Ile Gly Gln Ile Tyr Glu Thr Gln Phe Val Gly Ser Asn Asp
        195                 200                 205 cag ttg ttt att cat att gtg aaa gtc gca ctt ctt gtg att gcg att     672
Gln Leu Phe Ile His Ile Val Lys Val Ala Leu Leu Val Ile Ala Ile
    210                 215                 220 tta gca gtt att gtt gga gtt att ttc att cag caa gcc gta cgg aaa     720
Leu Ala Val Ile Val Gly Val Ile Phe Ile Gln Gln Ala Val Arg Lys
225                 230                 235                 240 att gcg att caa tat gct aaa ggc aca ggt cgt tca cct gct ggc gga     768
Ile Ala Ile Gln Tyr Ala Lys Gly Thr Gly Arg Ser Pro Ala Gly Gly
                245                 250                 255 ggt cag tct aca cac ctt cca ttg aaa gtg aat cct gca ggg gtt att     816
Gly Gln Ser Thr His Leu Pro Leu Lys Val Asn Pro Ala Gly Val Ile
            260                 265                 270 ccg gta atc ttt gcg gtt gcg ttt ttg ata acg ccg cgg acg atc gcg     864
Pro Val Ile Phe Ala Val Ala Phe Leu Ile Thr Pro Arg Thr Ile Ala
        275                 280                 285
```

```
tca ttc ttt gga aca aac gat gtg aca aag tgg att caa aac aac ttt    912
Ser Phe Phe Gly Thr Asn Asp Val Thr Lys Trp Ile Gln Asn Asn Phe
290                 295                 300 gat aat acg cat ccg gtg ggt atg gcg ata tat gtt gcg ttg att att    960
Asp Asn Thr His Pro Val Gly Met Ala Ile Tyr Val Ala Leu Ile Ile
305                 310                 315                 320 gcc ttt acg tac ttt tat gct ttt gta cag gta aac cct gaa caa atg   1008
Ala Phe Thr Tyr Phe Tyr Ala Phe Val Gln Val Asn Pro Glu Gln Met
                325                 330                 335 gct gat aac ctt aaa aaa cag ggt ggc tat atc ccg ggg gtt cgt cca   1056
Ala Asp Asn Leu Lys Lys Gln Gly Gly Tyr Ile Pro Gly Val Arg Pro
            340                 345                 350 ggg aaa atg act caa gat aga att acg agc att ttg tat cga ctt acg   1104
Gly Lys Met Thr Gln Asp Arg Ile Thr Ser Ile Leu Tyr Arg Leu Thr
        355                 360                 365 ttt gtg ggt tct ata ttc tta gcc gtg att tcc att ctt cct atc ttt   1152
Phe Val Gly Ser Ile Phe Leu Ala Val Ile Ser Ile Leu Pro Ile Phe
370                 375                 380 ttc att caa ttc gct gga ttg cct caa agt gca caa att ggc gga aca   1200
Phe Ile Gln Phe Ala Gly Leu Pro Gln Ser Ala Gln Ile Gly Gly Thr
385                 390                 395                 400 tct ttg tta att gtt gtc ggg gta gcc ttg gag aca atg aaa caa cta   1248
Ser Leu Leu Ile Val Val Gly Val Ala Leu Glu Thr Met Lys Gln Leu
                405                 410                 415 gaa agc cag ttg gtg aaa cga aac tac cgt gga ttt atg aaa aac tag   1296
Glu Ser Gln Leu Val Lys Arg Asn Tyr Arg Gly Phe Met Lys Asn
            420                 425                 430

<210> SEQ ID NO 2
<211> LENGTH: 431
<212> TYPE: PRT
<213> ORGANISM: Bacillus subtilis

<400> SEQUENCE: 2

Met Phe Lys Thr Ile Ser Asn Phe Met Arg Val Ser Asp Ile Arg Asn
1               5                   10                  15

Lys Ile Ile Phe Thr Leu Leu Met Leu Ile Val Phe Arg Ile Gly Ala
            20                  25                  30

Phe Ile Pro Val Pro Tyr Val Asn Ala Glu Ala Leu Gln Ala Gln Ser
        35                  40                  45

Gln Met Gly Val Phe Asp Leu Leu Asn Thr Phe Gly Gly Gly Ala Leu
    50                  55                  60

Tyr Gln Phe Ser Ile Phe Ala Met Gly Ile Thr Pro Tyr Ile Thr Ala
65                  70                  75                  80

Ser Ile Ile Ile Gln Leu Leu Gln Met Asp Val Val Pro Lys Phe Thr
                85                  90                  95

Glu Trp Ser Lys Gln Gly Glu Val Gly Arg Arg Lys Leu Ala Gln Phe
            100                 105                 110

Thr Arg Tyr Phe Thr Ile Val Leu Gly Phe Ile Gln Ala Leu Gly Met
        115                 120                 125

Ser Tyr Gly Phe Asn Asn Leu Ala Asn Gly Met Leu Ile Glu Lys Ser
    130                 135                 140

Gly Val Ser Thr Tyr Leu Ile Ile Ala Leu Val Leu Thr Gly Gly Thr
145                 150                 155                 160

Ala Phe Leu Met Trp Leu Gly Glu Gln Ile Thr Ser His Gly Val Gly
                165                 170                 175

Asn Gly Ile Ser Ile Ile Ile Phe Ala Gly Ile Val Ser Ile Pro
            180                 185                 190
```

```
Lys Thr Ile Gly Gln Ile Tyr Glu Thr Gln Phe Val Gly Ser Asn Asp
            195                 200                 205

Gln Leu Phe Ile His Ile Val Lys Val Ala Leu Leu Val Ile Ala Ile
            210                 215                 220

Leu Ala Val Ile Val Gly Val Ile Phe Ile Gln Gln Ala Val Arg Lys
225                 230                 235                 240

Ile Ala Ile Gln Tyr Ala Lys Gly Thr Gly Arg Ser Pro Ala Gly Gly
                245                 250                 255

Gly Gln Ser Thr His Leu Pro Leu Lys Val Asn Pro Ala Gly Val Ile
                260                 265                 270

Pro Val Ile Phe Ala Val Ala Phe Leu Ile Thr Pro Arg Thr Ile Ala
            275                 280                 285

Ser Phe Phe Gly Thr Asn Asp Val Thr Lys Trp Ile Gln Asn Asn Phe
            290                 295                 300

Asp Asn Thr His Pro Val Gly Met Ala Ile Tyr Val Ala Leu Ile Ile
305                 310                 315                 320

Ala Phe Thr Tyr Phe Tyr Ala Phe Val Gln Val Asn Pro Glu Gln Met
                325                 330                 335

Ala Asp Asn Leu Lys Lys Gln Gly Gly Tyr Ile Pro Gly Val Arg Pro
                340                 345                 350

Gly Lys Met Thr Gln Asp Arg Ile Thr Ser Ile Leu Tyr Arg Leu Thr
            355                 360                 365

Phe Val Gly Ser Ile Phe Leu Ala Val Ile Ser Ile Leu Pro Ile Phe
            370                 375                 380

Phe Ile Gln Phe Ala Gly Leu Pro Gln Ser Ala Gln Ile Gly Gly Thr
385                 390                 395                 400

Ser Leu Leu Ile Val Val Gly Val Ala Leu Glu Thr Met Lys Gln Leu
                405                 410                 415

Glu Ser Gln Leu Val Lys Arg Asn Tyr Arg Gly Phe Met Lys Asn
            420                 425                 430

<210> SEQ ID NO 3
<211> LENGTH: 1140
<212> TYPE: DNA
<213> ORGANISM: Bacillus sp. KSM-K16
<220> FEATURE:
<221> NAME/KEY: CDS
<222> LOCATION: (1)..(1140)

<400> SEQUENCE: 3 atg aag aaa ccg ttg ggg aaa att gtc gca agc acc gca cta ctc att     48
Met Lys Lys Pro Leu Gly Lys Ile Val Ala Ser Thr Ala Leu Leu Ile
1               5                   10                  15 tct gtt gct ttt agt tca tcg atc gca tcg gct gct gag gaa gca aaa     96
Ser Val Ala Phe Ser Ser Ser Ile Ala Ser Ala Ala Glu Glu Ala Lys
            20                  25                  30 gaa aaa tat tta att ggc ttt aat gag cag gaa gca gtt agt gag ttt    144
Glu Lys Tyr Leu Ile Gly Phe Asn Glu Gln Glu Ala Val Ser Glu Phe
        35                  40                  45 gta gag caa ata gag gca aat gac gat gtc gcg att ctc tct gag gaa    192
Val Glu Gln Ile Glu Ala Asn Asp Asp Val Ala Ile Leu Ser Glu Glu
    50                  55                  60 gag gaa gtc gaa att gaa ttg ctt cat gag ttt gaa acg att cct gtt    240
Glu Glu Val Glu Ile Glu Leu Leu His Glu Phe Glu Thr Ile Pro Val
65                  70                  75                  80 tta tct gtt gag tta agt cca gaa gat gtg gac gcg ctt gag ctc gat    288
Leu Ser Val Glu Leu Ser Pro Glu Asp Val Asp Ala Leu Glu Leu Asp
                85                  90                  95
```

```
cca acg att tcg tat att gaa gag gat gca gaa gta acg aca atg gcg      336
Pro Thr Ile Ser Tyr Ile Glu Glu Asp Ala Glu Val Thr Thr Met Ala
            100                 105                 110 caa tca gtg cca tgg gga att agc cgt gta caa gcc cca gct gcc cat      384
Gln Ser Val Pro Trp Gly Ile Ser Arg Val Gln Ala Pro Ala Ala His
        115                 120                 125 aac cgt gga ttg aca ggt tct ggt gta aaa gtt gct gtc ctc gat acg      432
Asn Arg Gly Leu Thr Gly Ser Gly Val Lys Val Ala Val Leu Asp Thr
130                 135                 140 ggt att tcc acc cat cca gac tta aat att cgc ggt ggt gct agc ttt      480
Gly Ile Ser Thr His Pro Asp Leu Asn Ile Arg Gly Gly Ala Ser Phe
145                 150                 155                 160 gtg cca gga gaa cca tcc act caa gat gga aat gga cat ggc acg cat      528
Val Pro Gly Glu Pro Ser Thr Gln Asp Gly Asn Gly His Gly Thr His
                165                 170                 175 gtg gca ggg acg att gct gct tta aac aat tcg att ggc gtt ctg ggc      576
Val Ala Gly Thr Ile Ala Ala Leu Asn Asn Ser Ile Gly Val Leu Gly
            180                 185                 190 gta gca ccg agc gcg gaa cta tac gct gta aaa gta tta ggc gcg agc      624
Val Ala Pro Ser Ala Glu Leu Tyr Ala Val Lys Val Leu Gly Ala Ser
        195                 200                 205 ggt tca ggt tcg gtc agc tcg att gcc caa gga ttg gaa tgg gca ggg      672
Gly Ser Gly Ser Val Ser Ser Ile Ala Gln Gly Leu Glu Trp Ala Gly
210                 215                 220 aac aat ggc atg cac gtt gcg aat ttg agt tta gga agc ccg tcg ccg      720
Asn Asn Gly Met His Val Ala Asn Leu Ser Leu Gly Ser Pro Ser Pro
225                 230                 235                 240 agt gca aca ctt gag caa gct gtt aat agc gct act tct aga ggc gtt      768
Ser Ala Thr Leu Glu Gln Ala Val Asn Ser Ala Thr Ser Arg Gly Val
                245                 250                 255 ctt gtc gta gca gca tct ggt aat tca ggt gca ggc tca atc agc tat      816
Leu Val Val Ala Ala Ser Gly Asn Ser Gly Ala Gly Ser Ile Ser Tyr
            260                 265                 270 ccg gcc cgt tat gcg aac gca atg gca gtc gga gcg act gac caa aac      864
Pro Ala Arg Tyr Ala Asn Ala Met Ala Val Gly Ala Thr Asp Gln Asn
        275                 280                 285 aac aac cgc gct agc ttt tca cag tat gga gct ggg ctt gac att gtc      912
Asn Asn Arg Ala Ser Phe Ser Gln Tyr Gly Ala Gly Leu Asp Ile Val
290                 295                 300 gcg cca ggt gtc aat gtg cag agc aca tac cca ggt tca aca tat gcc      960
Ala Pro Gly Val Asn Val Gln Ser Thr Tyr Pro Gly Ser Thr Tyr Ala
305                 310                 315                 320 agc tta aac ggt aca tcg atg gct act cct cat gtt gca ggt gta gca     1008
Ser Leu Asn Gly Thr Ser Met Ala Thr Pro His Val Ala Gly Val Ala
                325                 330                 335 gcc ctt gtt aaa caa aag aat cca tct tgg tcc aat gta caa atc cgc     1056
Ala Leu Val Lys Gln Lys Asn Pro Ser Trp Ser Asn Val Gln Ile Arg
            340                 345                 350 aat cat cta aag aat acg gca acg ggt tta gga aac acg aac ttg tat     1104
Asn His Leu Lys Asn Thr Ala Thr Gly Leu Gly Asn Thr Asn Leu Tyr
        355                 360                 365 gga agc ggg ctt gtc aat gca gaa gcg gca aca cgc                     1140
Gly Ser Gly Leu Val Asn Ala Glu Ala Ala Thr Arg
370                 375                 380

<210> SEQ ID NO 4
<211> LENGTH: 380
<212> TYPE: PRT
<213> ORGANISM: Bacillus sp. KSM-K16

<400> SEQUENCE: 4
```

```
Met Lys Lys Pro Leu Gly Lys Ile Val Ala Ser Thr Ala Leu Leu Ile
1               5                   10                  15

Ser Val Ala Phe Ser Ser Ile Ala Ser Ala Glu Glu Ala Lys
            20              25                  30

Glu Lys Tyr Leu Ile Gly Phe Asn Glu Gln Ala Val Ser Glu Phe
        35                  40                  45

Val Glu Gln Ile Glu Ala Asn Asp Val Ala Ile Leu Ser Glu Glu
    50                  55                  60

Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Thr Ile Ser Tyr Ile Glu Glu Asp Ala Glu Val Thr Thr Met Ala
                100                 105                 110

Gln Ser Val Pro Trp Gly Ile Ser Arg Val Gln Ala Pro Ala Ala His
            115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
                180                 185                 190

Val Ala Pro Ser Ala Glu Leu Tyr Ala Val Lys Val Leu Gly Ala Ser
            195                 200                 205

Gly Ser Gly Ser Val Ser Ser Ile Ala Gln Gly Leu Glu Trp Ala Gly
210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
                260                 265                 270

Pro Ala Arg Tyr Ala Asn Ala Met Ala Val Gly Ala Thr Asp Gln Asn
            275                 280                 285

Asn Asn Arg Ala Ser Phe Ser Gln Tyr Gly Ala Gly Leu Asp Ile Val
290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Val Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Gly Leu Gly Asn Thr Asn Leu Tyr
                355                 360                 365

Gly Ser Gly Leu Val Asn Ala Glu Ala Ala Thr Arg
370                 375                 380

<210> SEQ ID NO 5
<211> LENGTH: 3150
<212> TYPE: DNA
<213> ORGANISM: Bacillus sp. KSM-S237
<220> FEATURE:
<221> NAME/KEY: CDS
```

```
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..(3044)

<400> SEQUENCE: 5
gatttgccga tgcaacaggc ttatatttag aggaaatttc ttttaaatt gaatacggaa        60 taaaatcagg taaacaggtc ctgattttat tttttgagt ttttagaga actgaagatt       120 gaaataaaag tagaagacaa aggacataag aaaattgcat tagttttaat tatagaaaac       180 gccttttat aattatttat acctagaacg aaaatactgt ttcgaaagcg gtttactata       240
aaaccttata ttccggctct ttttaaaac aggggggtaaa aattcactct agtattctaa       300
tttcaacatg ctataataaa tttgtaagac gcaatatgca tctctttttt tacgatatat       360
gtaagcggtt aaccttgtgc tatatgccga tttaggaagg gggtagatt gagtcaagta       420 gtaataatat agataactta aagttgttg agaagcagga gagcatctgg ttactcaca       480 agttttttta aaactttaac gaaagcactt tcggtaatgc ttatgaattt agctatttga       540
ttcaattact ttaaaaatat ttaggaggta at atg atg tta aga aag aaa aca        593
                                   Met Met Leu Arg Lys Lys Thr
                                                         -25 aag cag ttg att tct tcc att ctt att tta gtt tta ctt cta tct tta        641
Lys Gln Leu Ile Ser Ser Ile Leu Ile Leu Val Leu Leu Leu Ser Leu
       -20              -15                  -10 ttt ccg gca gct ctt gca gca gaa gga aac act cgt gaa gac aat ttt        689
Phe Pro Ala Ala Leu Ala Ala Glu Gly Asn Thr Arg Glu Asp Asn Phe
-5                   -1  1               5                       10 aaa cat tta tta ggt aat gac aat gtt aaa cgc cct tct gag gct ggc        737
Lys His Leu Leu Gly Asn Asp Asn Val Lys Arg Pro Ser Glu Ala Gly
               15                  20                  25 gca tta caa tta caa gaa gtc gat gga caa atg aca tta gta gat caa        785
Ala Leu Gln Leu Gln Glu Val Asp Gly Gln Met Thr Leu Val Asp Gln
           30                  35                  40 cat gga gaa aaa att caa tta cgt gga atg agt aca cac gga tta cag        833
His Gly Glu Lys Ile Gln Leu Arg Gly Met Ser Thr His Gly Leu Gln
               45                  50                  55 tgg ttt cct gag atc ttg aat gat aac gca tac aaa gct ctt tct aac        881
Trp Phe Pro Glu Ile Leu Asn Asp Asn Ala Tyr Lys Ala Leu Ser Asn
       60                  65                  70 gat tgg gat tcc aat atg att cgt ctt gct atg tat gta ggt gaa aat        929
Asp Trp Asp Ser Asn Met Ile Arg Leu Ala Met Tyr Val Gly Glu Asn
75                  80                  85                  90 ggg tac gct aca aac cct gag tta atc aaa caa aga gtg att gat gga        977
Gly Tyr Ala Thr Asn Pro Glu Leu Ile Lys Gln Arg Val Ile Asp Gly
                95                  100                 105 att gag tta gcg att gaa aat gac atg tat gtt att gtt gac tgg cat       1025
Ile Glu Leu Ala Ile Glu Asn Asp Met Tyr Val Ile Val Asp Trp His
            110                 115                 120 gtt cat gcg cca ggt gat cct aga gat cct gtt tat gca ggt gct aaa       1073
Val His Ala Pro Gly Asp Pro Arg Asp Pro Val Tyr Ala Gly Ala Lys
            125                 130                 135 gat ttc ttt aga gaa att gca gct tta tac cct aat aat cca cac att       1121
Asp Phe Phe Arg Glu Ile Ala Ala Leu Tyr Pro Asn Asn Pro His Ile
        140                 145                 150 att tat gag tta gcg aat gag ccg agt agt aat aat aat ggt gga gca       1169
Ile Tyr Glu Leu Ala Asn Glu Pro Ser Ser Asn Asn Asn Gly Gly Ala
155                 160                 165                 170
```

```
ggg att ccg aat aac gaa gaa ggt tgg aaa gcg gta aaa gaa tat gct      1217
Gly Ile Pro Asn Asn Glu Glu Gly Trp Lys Ala Val Lys Glu Tyr Ala
            175                 180                 185 gat cca att gta gaa atg tta cgt aaa agc ggt aat gca gat gac aac      1265
Asp Pro Ile Val Glu Met Leu Arg Lys Ser Gly Asn Ala Asp Asp Asn
            190                 195                 200 att atc att gtt ggt agt cca aac tgg agt cag cgt ccg gac tta gca      1313
Ile Ile Ile Val Gly Ser Pro Asn Trp Ser Gln Arg Pro Asp Leu Ala
            205                 210                 215 gct gat aat cca att gat gat cac cat aca atg tat act gtt cac ttc      1361
Ala Asp Asn Pro Ile Asp Asp His His Thr Met Tyr Thr Val His Phe
            220                 225                 230 tac act ggt tca cat gct gct tca act gaa agc tat ccg tct gaa act      1409
Tyr Thr Gly Ser His Ala Ala Ser Thr Glu Ser Tyr Pro Ser Glu Thr
235                 240                 245                 250 cct aac tct gaa aga gga aac gta atg agt aac act cgt tat gcg tta      1457
Pro Asn Ser Glu Arg Gly Asn Val Met Ser Asn Thr Arg Tyr Ala Leu
            255                 260                 265 gaa aac gga gta gcg gta ttt gca aca gag tgg gga acg agt caa gct      1505
Glu Asn Gly Val Ala Val Phe Ala Thr Glu Trp Gly Thr Ser Gln Ala
            270                 275                 280 agt gga gac ggt ggt cct tac ttt gat gaa gca gat gta tgg att gaa      1553
Ser Gly Asp Gly Gly Pro Tyr Phe Asp Glu Ala Asp Val Trp Ile Glu
            285                 290                 295 ttt tta aat gaa aac aac att agc tgg gct aac tgg tct tta acg aat      1601
Phe Leu Asn Glu Asn Asn Ile Ser Trp Ala Asn Trp Ser Leu Thr Asn
            300                 305                 310 aaa aat gaa gta tct ggt gca ttt aca cca ttc gag tta ggt aag tct      1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa      1697
Asn Ala Thr Asn Leu Asp Pro Gly Pro Asp His Val Trp Ala Pro Glu
            335                 340                 345 gaa tta agt ctt tct gga gaa tat gta cgt gct cgt att aaa ggt gtg      1745
Glu Leu Ser Leu Ser Gly Glu Tyr Val Arg Ala Arg Ile Lys Gly Val
            350                 355                 360 aac tat gag cca atc gac cgt aca aaa tac acg aaa gta ctt tgg gac      1793
Asn Tyr Glu Pro Ile Asp Arg Thr Lys Tyr Thr Lys Val Leu Trp Asp
            365                 370                 375 ttt aat gat gga acg aag caa gga ttt gga gtg aat tcg gat tct cca      1841
Phe Asn Asp Gly Thr Lys Gln Gly Phe Gly Val Asn Ser Asp Ser Pro
380                 385                 390 aat aaa gaa ctt att gca gtt gat aat gaa aac aac act ttg aaa gtt      1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct      1937
Ser Gly Leu Asp Val Ser Asn Asp Val Ser Asp Gly Asn Phe Trp Ala
            415                 420                 425 aat gct cgt ctt tct gcc aac ggt tgg gga aaa agt gtt gat att tta      1985
Asn Ala Arg Leu Ser Ala Asn Gly Trp Gly Lys Ser Val Asp Ile Leu
            430                 435                 440 ggt gct gag aag ctt aca atg gat gtt att gtt gat gaa cca acg acg      2033
Gly Ala Glu Lys Leu Thr Met Asp Val Ile Val Asp Glu Pro Thr Thr
            445                 450                 455 gta gct att gcg gcg att cca caa agt agt aaa agt gga tgg gca aat      2081
Val Ala Ile Ala Ala Ile Pro Gln Ser Ser Lys Ser Gly Trp Ala Asn
            460                 465                 470 cca gag cgt gct gtt cga gtg aac gcg gaa gat ttt gtc cag caa acg      2129
Pro Glu Arg Ala Val Arg Val Asn Ala Glu Asp Phe Val Gln Gln Thr
475                 480                 485                 490
```

| | | | | | | | | | | | | | | | | |
|---|---|---|---|---|---|---|---|---|---|---|---|---|---|---|---|---|
| gac | ggt | aag | tat | aaa | gct | gga | tta | aca | att | aca | gga | gaa | gat | gct | cct | 2177 |
| Asp | Gly | Lys | Tyr | Lys | Ala | Gly | Leu | Thr | Ile | Thr | Gly | Glu | Asp | Ala | Pro | |
| | | | | 495 | | | | 500 | | | | | 505 | | | |
| aac | cta | aaa | aat | atc | gct | ttt | cat | gaa | gaa | gat | aac | aat | atg | aac | aac | 2225 |
| Asn | Leu | Lys | Asn | Ile | Ala | Phe | His | Glu | Glu | Asp | Asn | Asn | Met | Asn | Asn | |
| | | 510 | | | | | 515 | | | | | 520 | | | | |
| atc | att | ctg | ttc | gtg | gga | act | gat | gca | gct | gac | gtt | att | tac | tta | gat | 2273 |
| Ile | Ile | Leu | Phe | Val | Gly | Thr | Asp | Ala | Ala | Asp | Val | Ile | Tyr | Leu | Asp | |
| | | 525 | | | | | 530 | | | | | 535 | | | | |
| aac | att | aaa | gta | att | gga | aca | gaa | gtt | gaa | att | cca | gtt | gtt | cat | gat | 2321 |
| Asn | Ile | Lys | Val | Ile | Gly | Thr | Glu | Val | Glu | Ile | Pro | Val | Val | His | Asp | |
| | 540 | | | | | 545 | | | | | 550 | | | | | |
| cca | aaa | gga | gaa | gct | gtt | ctt | cct | tct | gtt | ttt | gaa | gac | ggt | aca | cgt | 2369 |
| Pro | Lys | Gly | Glu | Ala | Val | Leu | Pro | Ser | Val | Phe | Glu | Asp | Gly | Thr | Arg | |
| 555 | | | | | 560 | | | | | 565 | | | | | 570 | |
| caa | ggt | tgg | gac | tgg | gct | gga | gag | tct | ggt | gtg | aaa | aca | gct | tta | aca | 2417 |
| Gln | Gly | Trp | Asp | Trp | Ala | Gly | Glu | Ser | Gly | Val | Lys | Thr | Ala | Leu | Thr | |
| | | | | 575 | | | | | 580 | | | | | 585 | | |
| att | gaa | gaa | gca | aac | ggt | tct | aac | gcg | tta | tca | tgg | gaa | ttt | gga | tat | 2465 |
| Ile | Glu | Glu | Ala | Asn | Gly | Ser | Asn | Ala | Leu | Ser | Trp | Glu | Phe | Gly | Tyr | |
| | | | | 590 | | | | | 595 | | | | | 600 | | |
| cca | gaa | gta | aaa | cct | agt | gat | aac | tgg | gca | aca | gct | cca | cgt | tta | gat | 2513 |
| Pro | Glu | Val | Lys | Pro | Ser | Asp | Asn | Trp | Ala | Thr | Ala | Pro | Arg | Leu | Asp | |
| | | | 605 | | | | | 610 | | | | | 615 | | | |
| ttc | tgg | aaa | tct | gac | ttg | gtt | cgc | ggt | gag | aat | gat | tat | gta | gct | ttt | 2561 |
| Phe | Trp | Lys | Ser | Asp | Leu | Val | Arg | Gly | Glu | Asn | Asp | Tyr | Val | Ala | Phe | |
| | | 620 | | | | | 625 | | | | | 630 | | | | |
| gat | ttc | tat | cta | gat | cca | gtt | cgt | gca | aca | gaa | ggc | gca | atg | aat | atc | 2609 |
| Asp | Phe | Tyr | Leu | Asp | Pro | Val | Arg | Ala | Thr | Glu | Gly | Ala | Met | Asn | Ile | |
| 635 | | | | | 640 | | | | | 645 | | | | | 650 | |
| aat | tta | gta | ttc | cag | cca | cct | act | aac | ggg | tat | tgg | gta | caa | gca | cca | 2657 |
| Asn | Leu | Val | Phe | Gln | Pro | Pro | Thr | Asn | Gly | Tyr | Trp | Val | Gln | Ala | Pro | |
| | | | | 655 | | | | | 660 | | | | | 665 | | |
| aaa | acg | tat | acg | att | aac | ttt | gat | gaa | tta | gag | gaa | gcg | aat | caa | gta | 2705 |
| Lys | Thr | Tyr | Thr | Ile | Asn | Phe | Asp | Glu | Leu | Glu | Glu | Ala | Asn | Gln | Val | |
| | | | 670 | | | | | 675 | | | | | 680 | | | |
| aat | ggt | tta | tat | cac | tat | gaa | gtg | aaa | att | aac | gta | aga | gat | att | aca | 2753 |
| Asn | Gly | Leu | Tyr | His | Tyr | Glu | Val | Lys | Ile | Asn | Val | Arg | Asp | Ile | Thr | |
| | | | | 685 | | | | | 690 | | | | | 695 | | |
| aac | att | caa | gat | gac | acg | tta | cta | cgt | aac | atg | atg | atc | att | ttt | gca | 2801 |
| Asn | Ile | Gln | Asp | Asp | Thr | Leu | Leu | Arg | Asn | Met | Met | Ile | Ile | Phe | Ala | |
| | | | 700 | | | | | 705 | | | | | 710 | | | |
| gat | gta | gaa | agt | gac | ttt | gca | ggg | aga | gtc | ttt | gta | gat | aat | gtt | cgt | 2849 |
| Asp | Val | Glu | Ser | Asp | Phe | Ala | Gly | Arg | Val | Phe | Val | Asp | Asn | Val | Arg | |
| 715 | | | | | 720 | | | | | 725 | | | | | 730 | |
| ttt | gag | ggg | gct | gct | act | act | gag | ccg | gtt | gaa | cca | gag | cca | gtt | gat | 2897 |
| Phe | Glu | Gly | Ala | Ala | Thr | Thr | Glu | Pro | Val | Glu | Pro | Glu | Pro | Val | Asp | |
| | | | | 735 | | | | | 740 | | | | | 745 | | |
| cct | ggc | gaa | gag | acg | cca | cct | gtc | gat | gag | aag | gaa | gcg | aaa | aaa | gaa | 2945 |
| Pro | Gly | Glu | Glu | Thr | Pro | Pro | Val | Asp | Glu | Lys | Glu | Ala | Lys | Lys | Glu | |
| | | | 750 | | | | | 755 | | | | | 760 | | | |
| caa | aaa | gaa | gca | gag | aaa | gaa | gag | aaa | gaa | gca | gta | aaa | gaa | gaa | aag | 2993 |
| Gln | Lys | Glu | Ala | Glu | Lys | Glu | Glu | Lys | Glu | Ala | Val | Lys | Glu | Glu | Lys | |
| | | | | 765 | | | | | 770 | | | | | 775 | | |
| aaa | gaa | gct | aaa | gaa | gaa | aag | aaa | gca | gtc | aaa | aat | gag | gct | aag | aaa | 3041 |
| Lys | Glu | Ala | Lys | Glu | Glu | Lys | Lys | Ala | Val | Lys | Asn | Glu | Ala | Lys | Lys | |
| | | | | 780 | | | | | 785 | | | | | 790 | | |
| aaa | taatctatta | aactagttat | agggttatct | aaaggtctga | tgtagatctt | | | | | | | | | | | 3094 |
| Lys | | | | | | | | | | | | | | | | |
| 795 | | | | | | | | | | | | | | | | | ttagataacc tttttcttgc ataactggac acagagttgt tattaaagaa agtaag    3150

<210> SEQ ID NO 6
<211> LENGTH: 824
<212> TYPE: PRT
<213> ORGANISM: Bacillus sp. KSM-S237

<400> SEQUENCE: 6

```
Met Met Leu Arg Lys Lys Thr Lys Gln Leu Ile Ser Ser Ile Leu Ile
            -25                 -20                 -15
Leu Val Leu Leu Leu Ser Leu Phe Pro Ala Ala Leu Ala Ala Glu Gly
        -10                  -5              -1   1
Asn Thr Arg Glu Asp Asn Phe Lys His Leu Leu Gly Asn Asp Asn Val
     5                  10                  15
Lys Arg Pro Ser Glu Ala Gly Ala Leu Gln Leu Gln Glu Val Asp Gly
 20                  25                  30                  35
Gln Met Thr Leu Val Asp Gln His Gly Glu Lys Ile Gln Leu Arg Gly
             40                  45                  50
Met Ser Thr His Gly Leu Gln Trp Phe Pro Glu Ile Leu Asn Asp Asn
         55                  60                  65
Ala Tyr Lys Ala Leu Ser Asn Asp Trp Asp Ser Asn Met Ile Arg Leu
     70                  75                  80
Ala Met Tyr Val Gly Glu Asn Gly Tyr Ala Thr Asn Pro Glu Leu Ile
 85                  90                  95
Lys Gln Arg Val Ile Asp Gly Ile Glu Leu Ala Ile Glu Asn Asp Met
100                 105                 110                 115
Tyr Val Ile Val Asp Trp His Val His Ala Pro Gly Asp Pro Arg Asp
             120                 125                 130
Pro Val Tyr Ala Gly Ala Lys Asp Phe Phe Arg Glu Ile Ala Ala Leu
         135                 140                 145
Tyr Pro Asn Asn Pro His Ile Ile Tyr Glu Leu Ala Asn Glu Pro Ser
     150                 155                 160
Ser Asn Asn Asn Gly Gly Ala Gly Ile Pro Asn Asn Glu Glu Gly Trp
165                 170                 175
Lys Ala Val Lys Glu Tyr Ala Asp Pro Ile Val Glu Met Leu Arg Lys
180                 185                 190                 195
Ser Gly Asn Ala Asp Asp Asn Ile Ile Ile Val Gly Ser Pro Asn Trp
             200                 205                 210
Ser Gln Arg Pro Asp Leu Ala Ala Asp Asn Pro Ile Asp Asp His His
         215                 220                 225
Thr Met Tyr Thr Val His Phe Tyr Thr Gly Ser His Ala Ala Ser Thr
     230                 235                 240
Glu Ser Tyr Pro Ser Glu Thr Pro Asn Ser Glu Arg Gly Asn Val Met
245                 250                 255
Ser Asn Thr Arg Tyr Ala Leu Glu Asn Gly Val Ala Val Phe Ala Thr
260                 265                 270                 275
Glu Trp Gly Thr Ser Gln Ala Ser Gly Asp Gly Gly Pro Tyr Phe Asp
             280                 285                 290
Glu Ala Asp Val Trp Ile Glu Phe Leu Asn Glu Asn Asn Ile Ser Trp
         295                 300                 305
Ala Asn Trp Ser Leu Thr Asn Lys Asn Glu Val Ser Gly Ala Phe Thr
     310                 315                 320
Pro Phe Glu Leu Gly Lys Ser Asn Ala Thr Asn Leu Asp Pro Gly Pro
325                 330                 335
Asp His Val Trp Ala Pro Glu Glu Leu Ser Leu Ser Gly Glu Tyr Val
```

-continued

```
              340                 345                 350                 355
Arg Ala Arg Ile Lys Gly Val Asn Tyr Glu Pro Ile Asp Arg Thr Lys
              360                 365                 370
Tyr Thr Lys Val Leu Trp Asp Phe Asn Asp Gly Thr Lys Gln Gly Phe
              375                 380                 385
Gly Val Asn Ser Asp Ser Pro Asn Lys Glu Leu Ile Ala Val Asp Asn
              390                 395                 400
Glu Asn Asn Thr Leu Lys Val Ser Gly Leu Asp Val Ser Asn Asp Val
              405                 410                 415
Ser Asp Gly Asn Phe Trp Ala Asn Ala Arg Leu Ser Ala Asn Gly Trp
420                 425                 430                 435
Gly Lys Ser Val Asp Ile Leu Gly Ala Glu Lys Leu Thr Met Asp Val
              440                 445                 450
Ile Val Asp Glu Pro Thr Thr Val Ala Ile Ala Ile Pro Gln Ser
              455                 460                 465
Ser Lys Ser Gly Trp Ala Asn Pro Glu Arg Ala Val Arg Val Asn Ala
              470                 475                 480
Glu Asp Phe Val Gln Gln Thr Asp Gly Lys Tyr Lys Ala Gly Leu Thr
              485                 490                 495
Ile Thr Gly Glu Asp Ala Pro Asn Leu Lys Asn Ile Ala Phe His Glu
500                 505                 510                 515
Glu Asp Asn Asn Met Asn Asn Ile Ile Leu Phe Val Gly Thr Asp Ala
              520                 525                 530
Ala Asp Val Ile Tyr Leu Asp Asn Ile Lys Val Ile Gly Thr Glu Val
              535                 540                 545
Glu Ile Pro Val Val His Asp Pro Lys Gly Glu Ala Val Leu Pro Ser
              550                 555                 560
Val Phe Glu Asp Gly Thr Arg Gln Gly Trp Asp Trp Ala Gly Glu Ser
              565                 570                 575
Gly Val Lys Thr Ala Leu Thr Ile Glu Glu Ala Asn Gly Ser Asn Ala
580                 585                 590                 595
Leu Ser Trp Glu Phe Gly Tyr Pro Glu Val Lys Pro Ser Asp Asn Trp
              600                 605                 610
Ala Thr Ala Pro Arg Leu Asp Phe Trp Lys Ser Asp Leu Val Arg Gly
              615                 620                 625
Glu Asn Asp Tyr Val Ala Phe Asp Phe Tyr Leu Asp Pro Val Arg Ala
              630                 635                 640
Thr Glu Gly Ala Met Asn Ile Asn Leu Val Phe Gln Pro Pro Thr Asn
              645                 650                 655
Gly Tyr Trp Val Gln Ala Pro Lys Thr Tyr Thr Ile Asn Phe Asp Glu
660                 665                 670                 675
Leu Glu Glu Ala Asn Gln Val Asn Gly Leu Tyr His Tyr Glu Val Lys
              680                 685                 690
Ile Asn Val Arg Asp Ile Thr Asn Ile Gln Asp Thr Leu Leu Arg
              695                 700                 705
Asn Met Met Ile Ile Phe Ala Asp Val Glu Ser Asp Phe Ala Gly Arg
              710                 715                 720
Val Phe Val Asp Asn Val Arg Phe Glu Gly Ala Ala Thr Thr Glu Pro
              725                 730                 735
Val Glu Pro Glu Pro Val Asp Pro Gly Glu Glu Thr Pro Pro Val Asp
              740                 745                 750                 755
Glu Lys Glu Ala Lys Lys Glu Gln Lys Glu Ala Glu Lys Glu Glu Lys
              760                 765                 770
```

Glu Ala Val Lys Glu Glu Lys Lys Glu Ala Lys Glu Lys Lys Ala
              775                 780                 785

Val Lys Asn Glu Ala Lys Lys Lys
        790                 795

<210> SEQ ID NO 7
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..(3075)

<400> SEQUENCE: 7

| | |
|---|---|
| agtacttacc attttagagt caaaagatag aagccaagca ggatttgccg atgcaaccgg | 60 |
| cttatattta gagggaattt cttttttaaat tgaatacgga ataaaatcag gtaaacaggt | 120 |
| cctgatttta tttttttgaa ttttttttgag aactaaagat tgaaatagaa gtagaagaca | 180 |
| acggacataa gaaaattgta ttagttttaa ttatagaaaa cgcttttcta taattattta | 240 |
| tacctagaac gaaaatactg tttcgaaagc ggtttactat aaaaccttat attccggctc | 300 |
| tttttttaaa caggggggtga aaattcactc tagtattcta atttcaacat gctataataa | 360 |
| atttgtaaga cgcaatatac atcttttttt tatgatattt gtaagcggtt aaccttgtgc | 420 |
| tatatgccga tttaggaagg gggtagattg agtcaagtag tcataattta gataacttat | 480 |
| aagttgttga gaagcaggag agaatctggg ttactcacaa gttttttaaa acattatcga | 540 |
| aagcactttc ggttatgctt atgaatttag ctatttgatt caattacttt aataatttta | 600 |

| | | |
|---|---|---|
| ggaggtaat atg atg tta aga aag aaa aca aag cag ttg att tct tcc att | | 651 |
| Met Met Leu Arg Lys Lys Thr Lys Gln Leu Ile Ser Ser Ile | | |
| -25 -20 | | |

| | | |
|---|---|---|
| ctt att tta gtt tta ctt cta tct tta ttt ccg aca gct ctt gca gca | | 699 |
| Leu Ile Leu Val Leu Leu Leu Ser Leu Phe Pro Thr Ala Leu Ala Ala | | |
| -15 -10 -5 -1 1 | | |

| | | |
|---|---|---|
| gaa gga aac act cgt gaa gac aat ttt aaa cat tta tta ggt aat gac | | 747 |
| Glu Gly Asn Thr Arg Glu Asp Asn Phe Lys His Leu Leu Gly Asn Asp | | |
| 5 10 15 | | |

| | | |
|---|---|---|
| aat gtt aaa cgc cct tct gag gct ggc gca tta caa tta caa gaa gtc | | 795 |
| Asn Val Lys Arg Pro Ser Glu Ala Gly Ala Leu Gln Leu Gln Glu Val | | |
| 20 25 30 | | |

| | | |
|---|---|---|
| gat gga caa atg aca tta gta gat caa cat gga gaa aaa att caa tta | | 843 |
| Asp Gly Gln Met Thr Leu Val Asp Gln His Gly Glu Lys Ile Gln Leu | | |
| 35 40 45 | | |

| | | |
|---|---|---|
| cgt gga atg agt aca cac gga tta caa tgg ttt cct gag atc ttg aat | | 891 |
| Arg Gly Met Ser Thr His Gly Leu Gln Trp Phe Pro Glu Ile Leu Asn | | |
| 50 55 60 65 | | |

| | | |
|---|---|---|
| gat aac gca tac aaa gct ctt gct aac gat tgg gaa tca aat atg att | | 939 |
| Asp Asn Ala Tyr Lys Ala Leu Ala Asn Asp Trp Glu Ser Asn Met Ile | | |
| 70 75 80 | | |

| | | |
|---|---|---|
| cgt cta gct atg tat gtc ggt gaa aat ggc tat gct tca aat cca gag | | 987 |
| Arg Leu Ala Met Tyr Val Gly Glu Asn Gly Tyr Ala Ser Asn Pro Glu | | |
| 85 90 95 | | |

| | | |
|---|---|---|
| tta att aaa agc aga gtc att aaa gga ata gat ctt gct att gaa aat | | 1035 |
| Leu Ile Lys Ser Arg Val Ile Lys Gly Ile Asp Leu Ala Ile Glu Asn | | |
| 100 105 110 | | |

| | | |
|---|---|---|
| gac atg tat gtc atc gtt gat tgg cat gta cat gca cct ggt gat cct | | 1083 |

```
             Asp Met Tyr Val Ile Val Asp Trp His Val His Ala Pro Gly Asp Pro
                 115                 120                 125 aga gat ccc gtt tac gct gga gca gaa gat ttc ttt aga gat att gca     1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag     1179
Ala Leu Tyr Pro Asn Asn Pro His Ile Ile Tyr Glu Leu Ala Asn Glu
                150                 155                 160 cca agt agt aac aat aat ggt gga gct ggg att cca aat aat gaa gaa     1227
Pro Ser Ser Asn Asn Asn Gly Gly Ala Gly Ile Pro Asn Asn Glu Glu
            165                 170                 175 ggt tgg aat gcg gta aaa gaa tac gct gat cca att gta gaa atg tta     1275
Gly Trp Asn Ala Val Lys Glu Tyr Ala Asp Pro Ile Val Glu Met Leu
        180                 185                 190 cgt gat agc ggg aac gca gat gac aat att atc att gtg ggt agt cca     1323
Arg Asp Ser Gly Asn Ala Asp Asp Asn Ile Ile Ile Val Gly Ser Pro
    195                 200                 205 aac tgg agt cag cgt cct gac tta gca gct gat aat cca att gat gat     1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct     1419
His His Thr Met Tyr Thr Val His Phe Tyr Thr Gly Ser His Ala Ala
                230                 235                 240 tca act gaa agc tat ccg cct gaa act cct aac tct gaa aga gga aac     1467
Ser Thr Glu Ser Tyr Pro Pro Glu Thr Pro Asn Ser Glu Arg Gly Asn
            245                 250                 255 gta atg agt aac act cgt tat gcg tta gaa aac gga gta gca gta ttt     1515
Val Met Ser Asn Thr Arg Tyr Ala Leu Glu Asn Gly Val Ala Val Phe
        260                 265                 270 gca aca gag tgg gga act agc caa gca aat gga gat ggt ggt cct tac     1563
Ala Thr Glu Trp Gly Thr Ser Gln Ala Asn Gly Asp Gly Gly Pro Tyr
    275                 280                 285 ttt gat gaa gca gat gta tgg att gag ttt tta aat gaa aac aac att     1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca     1659
Ser Trp Ala Asn Trp Ser Leu Thr Asn Lys Asn Glu Val Ser Gly Ala
                310                 315                 320 ttt aca cca ttc gag tta ggt aag tct aac gca aca agt ctt gac cca     1707
Phe Thr Pro Phe Glu Leu Gly Lys Ser Asn Ala Thr Ser Leu Asp Pro
            325                 330                 335 ggg cca gac caa gta tgg gta cca gaa gag tta agt ctt tct gga gaa     1755
Gly Pro Asp Gln Val Trp Val Pro Glu Glu Leu Ser Leu Ser Gly Glu
        340                 345                 350 tat gta cgt gct cgt att aaa ggt gtg aac tat gag cca atc gac cgt     1803
Tyr Val Arg Ala Arg Ile Lys Gly Val Asn Tyr Glu Pro Ile Asp Arg
    355                 360                 365 aca aaa tac acg aaa gta ctt tgg gac ttt aat gat gga acg aag caa     1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag     1899
Gly Phe Gly Val Asn Gly Asp Ser Pro Val Glu Asp Val Val Ile Glu
                390                 395                 400 aat gaa gcg ggc gct tta aaa ctt tca gga tta gat gca agt aat gat     1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt     1995
Val Ser Glu Gly Asn Tyr Trp Ala Asn Ala Arg Leu Ser Ala Asp Gly
        420                 425                 430 tgg gga aaa agt gtt gat att tta ggt gct gaa aaa ctt act atg gat     2043
```

-continued

| | | | | | | | | | | | | | | |
|---|---|---|---|---|---|---|---|---|---|---|---|---|---|---|
| Trp | Gly | Lys | Ser | Val | Asp | Ile | Leu | Gly | Ala | Glu | Lys | Leu | Thr | Met | Asp |
| | 435 | | | | 440 | | | | | 445 | | | | | |

| gtg | att | gtt | gat | gag | ccg | acc | acg | gta | tca | att | gct | gca | att | cca | caa | 2091 |
|---|---|---|---|---|---|---|---|---|---|---|---|---|---|---|---|---|
| Val | Ile | Val | Asp | Glu | Pro | Thr | Thr | Val | Ser | Ile | Ala | Ala | Ile | Pro | Gln | |
| 450 | | | | | 455 | | | | | 460 | | | | | 465 | |

| ggg | cca | tca | gcc | aat | tgg | gtt | aat | cca | aat | cgt | gca | att | aag | gtt | gag | 2139 |
|---|---|---|---|---|---|---|---|---|---|---|---|---|---|---|---|---|
| Gly | Pro | Ser | Ala | Asn | Trp | Val | Asn | Pro | Asn | Arg | Ala | Ile | Lys | Val | Glu | |
| | | | | 470 | | | | | 475 | | | | | 480 | | |

| cca | act | aat | ttc | gta | ccg | tta | gga | gat | aag | ttt | aaa | gcg | gaa | tta | act | 2187 |
|---|---|---|---|---|---|---|---|---|---|---|---|---|---|---|---|---|
| Pro | Thr | Asn | Phe | Val | Pro | Leu | Gly | Asp | Lys | Phe | Lys | Ala | Glu | Leu | Thr | |
| | | | 485 | | | | | 490 | | | | | 495 | | | |

| ata | act | tca | gct | gac | tct | cca | tcg | tta | gaa | gct | att | gcg | atg | cat | gct | 2235 |
|---|---|---|---|---|---|---|---|---|---|---|---|---|---|---|---|---|
| Ile | Thr | Ser | Ala | Asp | Ser | Pro | Ser | Leu | Glu | Ala | Ile | Ala | Met | His | Ala | |
| | | | 500 | | | | | 505 | | | | | 510 | | | |

| gaa | aat | aac | aac | atc | aac | aac | atc | att | ctt | ttt | gta | gga | act | gaa | ggt | 2283 |
|---|---|---|---|---|---|---|---|---|---|---|---|---|---|---|---|---|
| Glu | Asn | Asn | Asn | Ile | Asn | Asn | Ile | Ile | Leu | Phe | Val | Gly | Thr | Glu | Gly | |
| 515 | | | | | 520 | | | | | 525 | | | | | | |

| gct | gat | gtt | atc | tat | tta | gat | aac | att | aaa | gta | att | gga | aca | gaa | gtt | 2331 |
|---|---|---|---|---|---|---|---|---|---|---|---|---|---|---|---|---|
| Ala | Asp | Val | Ile | Tyr | Leu | Asp | Asn | Ile | Lys | Val | Ile | Gly | Thr | Glu | Val | |
| 530 | | | | | 535 | | | | | 540 | | | | | 545 | |

| gaa | att | cca | gtt | gtt | cat | gat | cca | aaa | gga | gaa | gct | gtt | ctt | cct | tct | 2379 |
|---|---|---|---|---|---|---|---|---|---|---|---|---|---|---|---|---|
| Glu | Ile | Pro | Val | Val | His | Asp | Pro | Lys | Gly | Glu | Ala | Val | Leu | Pro | Ser | |
| | | | | 550 | | | | | 555 | | | | | 560 | | |

| gtt | ttt | gaa | gac | ggt | aca | cgt | caa | ggt | tgg | gac | tgg | gct | gga | gag | tct | 2427 |
|---|---|---|---|---|---|---|---|---|---|---|---|---|---|---|---|---|
| Val | Phe | Glu | Asp | Gly | Thr | Arg | Gln | Gly | Trp | Asp | Trp | Ala | Gly | Glu | Ser | |
| | | | 565 | | | | | 570 | | | | | 575 | | | |

| ggt | gtg | aaa | aca | gct | tta | aca | att | gaa | gaa | gca | aac | ggt | tct | aac | gcg | 2475 |
|---|---|---|---|---|---|---|---|---|---|---|---|---|---|---|---|---|
| Gly | Val | Lys | Thr | Ala | Leu | Thr | Ile | Glu | Glu | Ala | Asn | Gly | Ser | Asn | Ala | |
| | | 580 | | | | | 585 | | | | | 590 | | | | |

| tta | tca | tgg | gaa | ttt | gga | tac | cca | gaa | gta | aaa | cct | agt | gat | aac | tgg | 2523 |
|---|---|---|---|---|---|---|---|---|---|---|---|---|---|---|---|---|
| Leu | Ser | Trp | Glu | Phe | Gly | Tyr | Pro | Glu | Val | Lys | Pro | Ser | Asp | Asn | Trp | |
| 595 | | | | | 600 | | | | | 605 | | | | | | |

| gca | aca | gct | cca | cgt | tta | gat | ttc | tgg | aaa | tct | gac | ttg | gtt | cgc | ggt | 2571 |
|---|---|---|---|---|---|---|---|---|---|---|---|---|---|---|---|---|
| Ala | Thr | Ala | Pro | Arg | Leu | Asp | Phe | Trp | Lys | Ser | Asp | Leu | Val | Arg | Gly | |
| 610 | | | | | 615 | | | | | 620 | | | | | 625 | |

| gaa | aat | gat | tat | gta | act | ttt | gat | ttc | tat | cta | gat | cca | gtt | cgt | gca | 2619 |
|---|---|---|---|---|---|---|---|---|---|---|---|---|---|---|---|---|
| Glu | Asn | Asp | Tyr | Val | Thr | Phe | Asp | Phe | Tyr | Leu | Asp | Pro | Val | Arg | Ala | |
| | | | | 630 | | | | | 635 | | | | | 640 | | |

| aca | gaa | ggc | gca | atg | aat | atc | aat | tta | gta | ttc | cag | cca | cct | act | aac | 2667 |
|---|---|---|---|---|---|---|---|---|---|---|---|---|---|---|---|---|
| Thr | Glu | Gly | Ala | Met | Asn | Ile | Asn | Leu | Val | Phe | Gln | Pro | Pro | Thr | Asn | |
| | | | | 645 | | | | | 650 | | | | | 655 | | |

| ggg | tat | tgg | gta | caa | gca | cca | aaa | acg | tat | acg | att | aac | ttt | gat | gaa | 2715 |
|---|---|---|---|---|---|---|---|---|---|---|---|---|---|---|---|---|
| Gly | Tyr | Trp | Val | Gln | Ala | Pro | Lys | Thr | Tyr | Thr | Ile | Asn | Phe | Asp | Glu | |
| | | | 660 | | | | | 665 | | | | | 670 | | | |

| tta | gag | gaa | gcg | aat | caa | gta | aat | ggt | tta | tat | cac | tat | gaa | gtg | aaa | 2763 |
|---|---|---|---|---|---|---|---|---|---|---|---|---|---|---|---|---|
| Leu | Glu | Glu | Ala | Asn | Gln | Val | Asn | Gly | Leu | Tyr | His | Tyr | Glu | Val | Lys | |
| | 675 | | | | | 680 | | | | | 685 | | | | | |

| att | aac | gta | aga | gat | att | aca | aac | att | caa | gat | gac | acg | tta | cta | cgt | 2811 |
|---|---|---|---|---|---|---|---|---|---|---|---|---|---|---|---|---|
| Ile | Asn | Val | Arg | Asp | Ile | Thr | Asn | Ile | Gln | Asp | Asp | Thr | Leu | Leu | Arg | |
| 690 | | | | | 695 | | | | | 700 | | | | | 705 | |

| aac | atg | atg | atc | att | ttt | gca | gat | gta | gaa | agt | gac | ttt | gca | ggg | aga | 2859 |
|---|---|---|---|---|---|---|---|---|---|---|---|---|---|---|---|---|
| Asn | Met | Met | Ile | Ile | Phe | Ala | Asp | Val | Glu | Ser | Asp | Phe | Ala | Gly | Arg | |
| | | | | 710 | | | | | 715 | | | | | 720 | | |

| gtc | ttt | gta | gat | aat | gtt | cgt | ttt | gag | ggg | gct | gct | act | act | gag | ccg | 2907 |
|---|---|---|---|---|---|---|---|---|---|---|---|---|---|---|---|---|
| Val | Phe | Val | Asp | Asn | Val | Arg | Phe | Glu | Gly | Ala | Ala | Thr | Thr | Glu | Pro | |
| | | | 725 | | | | | 730 | | | | | 735 | | | |

| gtt | gaa | cca | gag | cca | gtt | gat | cct | ggc | gaa | gag | acg | ccg | cct | gtc | gat | 2955 |
|---|---|---|---|---|---|---|---|---|---|---|---|---|---|---|---|---|
| Val | Glu | Pro | Glu | Pro | Val | Asp | Pro | Gly | Glu | Glu | Thr | Pro | Pro | Val | Asp | |
| | | 740 | | | | | 745 | | | | | 750 | | | | |

| gag | aag | gaa | gcg | aaa | aaa | gaa | caa | aaa | gaa | gca | gag | aaa | gaa | gag | aaa | 3003 |

-continued

```
Glu Lys Glu Ala Lys Lys Glu Gln Lys Glu Ala Gly Lys Glu Glu Lys
            755                 760                 765 gaa gca gta aaa gaa gaa aag aaa gaa gct aaa gaa gaa aag aaa gca       3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct      3105
Ile Lys Asn Glu Ala Thr Lys Lys
                790 aaaggtctga tgcagatctt ttagataacc ttttttttgca taactggaca tagaatggtt    3165 attaaagaaa gcaaggtgtt tatacgatat taaaaaggta gcgatttttaa attgaaacct    3225 ttaataatgt cttgtgatag aatgatgaag taatttaaga gggggaaacg aagtgaaaac     3285 ggaaatttct agtagaagaa aaacagacca agaaatactg caagctt                   3332

<210> SEQ ID NO 8
<211> LENGTH: 822
<212> TYPE: PRT
<213> ORGANISM: Bacillus sp. KSM-64

<400> SEQUENCE: 8

Met Met Leu Arg Lys Lys Thr Lys Gln Leu Ile Ser Ser Ile Leu Ile
            -25                 -20                 -15

Leu Val Leu Leu Leu Ser Leu Phe Pro Thr Ala Leu Ala Ala Glu Gly
        -10                  -5              -1   1

Asn Thr Arg Glu Asp Asn Phe Lys His Leu Leu Gly Asn Asp Asn Val
         5                  10                  15

Lys Arg Pro Ser Glu Ala Gly Ala Leu Gln Leu Gln Glu Val Asp Gly
20                  25                  30                  35

Gln Met Thr Leu Val Asp Gln His Gly Glu Lys Ile Gln Leu Arg Gly
                40                  45                  50

Met Ser Thr His Gly Leu Gln Trp Phe Pro Glu Ile Leu Asn Asp Asn
            55                  60                  65

Ala Tyr Lys Ala Leu Ala Asn Asp Trp Glu Ser Asn Met Ile Arg Leu
        70                  75                  80

Ala Met Tyr Val Gly Glu Asn Gly Tyr Ala Ser Asn Pro Glu Leu Ile
    85                  90                  95

Lys Ser Arg Val Ile Lys Gly Ile Asp Leu Ala Ile Glu Asn Asp Met
100                 105                 110                 115

Tyr Val Ile Val Asp Trp His Val His Ala Pro Gly Asp Pro Arg Asp
                120                 125                 130

Pro Val Tyr Ala Gly Ala Glu Asp Phe Phe Arg Asp Ile Ala Ala Leu
            135                 140                 145

Tyr Pro Asn Asn Pro His Ile Ile Tyr Glu Leu Ala Asn Glu Pro Ser
        150                 155                 160

Ser Asn Asn Asn Gly Gly Ala Gly Ile Pro Asn Asn Glu Glu Gly Trp
    165                 170                 175

Asn Ala Val Lys Glu Tyr Ala Asp Pro Ile Val Glu Met Leu Arg Asp
180                 185                 190                 195

Ser Gly Asn Ala Asp Asp Asn Ile Ile Ile Val Gly Ser Pro Asn Trp
                200                 205                 210

Ser Gln Arg Pro Asp Leu Ala Ala Asp Asn Pro Ile Asp Asp His His
            215                 220                 225

Thr Met Tyr Thr Val His Phe Tyr Thr Gly Ser His Ala Ala Ser Thr
        230                 235                 240

Glu Ser Tyr Pro Pro Glu Thr Pro Asn Ser Glu Arg Gly Asn Val Met
    245                 250                 255
```

-continued

Ser Asn Thr Arg Tyr Ala Leu Glu Asn Gly Val Ala Val Phe Ala Thr
260                 265                 270                 275

Glu Trp Gly Thr Ser Gln Ala Asn Gly Asp Gly Pro Tyr Phe Asp
            280                 285                 290

Glu Ala Asp Val Trp Ile Glu Phe Leu Asn Glu Asn Asn Ile Ser Trp
                295                 300                 305

Ala Asn Trp Ser Leu Thr Asn Lys Asn Glu Val Ser Gly Ala Phe Thr
        310                 315                 320

Pro Phe Glu Leu Gly Lys Ser Asn Ala Thr Ser Leu Asp Pro Gly Pro
            325                 330                 335

Asp Gln Val Trp Val Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
                360                 365                 370

Tyr Thr Lys Val Leu Trp Asp Phe Asn Asp Gly Thr Lys Gln Gly Phe
            375                 380                 385

Gly Val Asn Gly Asp Ser Pro Val Glu Asp Val Val Ile Glu Asn Glu
        390                 395                 400

Ala Gly Ala Leu Lys Leu Ser Gly Leu Asp Ala Ser Asn Asp Val Ser
405                 410                 415

Glu Gly Asn Tyr Trp Ala Asn Ala Arg Leu Ser Ala Asp Gly Trp Gly
420                 425                 430                 435

Lys Ser Val Asp Ile Leu Gly Ala Glu Lys Leu Thr Met Asp Val Ile
                440                 445                 450

Val Asp Glu Pro Thr Thr Val Ser Ile Ala Ala Ile Pro Gln Gly Pro
            455                 460                 465

Ser Ala Asn Trp Val Asn Pro Asn Arg Ala Ile Lys Val Glu Pro Thr
        470                 475                 480

Asn Phe Val Pro Leu Gly Asp Lys Phe Lys Ala Glu Leu Thr Ile Thr
    485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
            520                 525                 530

Val Ile Tyr Leu Asp Asn Ile Lys Val Ile Gly Thr Glu Val Glu Ile
        535                 540                 545

Pro Val Val His Asp Pro Lys Gly Glu Ala Val Leu Pro Ser Val Phe
    550                 555                 560

Glu Asp Gly Thr Arg Gln Gly Trp Asp Trp Ala Gly Glu Ser Gly Val
565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
            600                 605                 610

Ala Pro Arg Leu Asp Phe Trp Lys Ser Asp Leu Val Arg Gly Glu Asn
        615                 620                 625

Asp Tyr Val Thr Phe Asp Phe Tyr Leu Asp Pro Val Arg Ala Thr Glu
    630                 635                 640

Gly Ala Met Asn Ile Asn Leu Val Phe Gln Pro Thr Asn Gly Tyr
645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn

```
                         680                685                690
Val Arg Asp Ile Thr Asn Ile Gln Asp Asp Thr Leu Leu Arg Asn Met
                    695                700                705

Met Ile Ile Phe Ala Asp Val Glu Ser Asp Phe Ala Gly Arg Val Phe
                710                715                720

Val Asp Asn Val Arg Phe Glu Gly Ala Ala Thr Thr Glu Pro Val Glu
            725                730                735

Pro Glu Pro Val Asp Pro Gly Glu Glu Thr Pro Pro Val Asp Glu Lys
740                745                750                755

Glu Ala Lys Lys Glu Gln Lys Glu Ala Glu Lys Glu Glu Lys Glu Ala
                760                765                770

Val Lys Glu Glu Lys Lys Glu Ala Lys Glu Glu Lys Lys Ala Ile Lys
            775                780                785

Asn Glu Ala Thr Lys Lys
        790

<210> SEQ ID NO 9
<211> LENGTH: 230
<212> TYPE: DNA
<213> ORGANISM: Bacillus subtilis

<400> SEQUENCE: 9
gttagtcgag atcgaagtta ttgcactggt gaaataataa gaaaagtgat tctgggagag    60
ccgggatcac ttttttattt accttatgcc cgaaatgaaa gctttatgac ctaattgtgt   120
aactatatcc tatttttttca aaaatatttt taaaaacgag caggatttca gaaaaaatcg   180
tggaattgat acactaatgc ttttatatag ggaaaaggtg gtgaactact              230

<210> SEQ ID NO 10
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region of Bacillus
      subtilis gene, spoVG

<400> SEQUENCE: 10
gttagtcgag atcgaagtta                                                 20

<210> SEQ ID NO 11
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region of Bacillus
      subtilis gene, spoVG

<400> SEQUENCE: 11
agtagttcac cacctttttcc                                                20

<210> SEQ ID NO 12
<211> LENGTH: 43
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secY and a 5'-portion designed from the nucleotide sequence of
      5'-flanking region of Bacillus subtilis gene, spoVG

<400> SEQUENCE: 12
```

```
ggaaaaggtg gtgaactact atgttgttta aaacaatctc caa          43
```

<210> SEQ ID NO 13
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secY and a 5'-portion designed from the nucleotide sequence of
      chloramphenicol resistant gene

<400> SEQUENCE: 13

```
atgggtgctt tagttgaaga ctagtttttc ataaatccac              40
```

<210> SEQ ID NO 14
<211> LENGTH: 19
<212> TYPE: DNA
<213> ORGANISM: Artificial sequence
<220> FEATURE:
<223> OTHER INFORMATION: Oligonucleotide as forward PCR primer for
      amplification of chloramphenicol resistant gene

<400> SEQUENCE: 14

```
caactaaagc acccattag                                     19
```

<210> SEQ ID NO 15
<211> LENGTH: 18
<212> TYPE: DNA
<213> ORGANISM: Artificial sequence
<220> FEATURE:
<223> OTHER INFORMATION: Oligonucleotide as forward PCR primer for
      amplification of chloramphenicol resistant gene

<400> SEQUENCE: 15

```
cttcaactaa cggggcag                                      18
```

<210> SEQ ID NO 16
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region of Bacillus subtilis
      gene, spoVG

<400> SEQUENCE: 16

```
taagaaaagt gattctggga                                    20
```

<210> SEQ ID NO 17
<211> LENGTH: 21
<212> TYPE: DNA
<213> ORGANISM: Artificial sequence
<220> FEATURE:
<223> OTHER INFORMATION: Oligonucleotide as reverse PCR primer for
      amplification of chloramphenicol resistant gene

<400> SEQUENCE: 17

```
ctcatattat aaaagccagt c                                  21
```

<210> SEQ ID NO 18
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of Bacillus subtilis gene, amyE

<400> SEQUENCE: 18
ggagtgtcaa gaatgtttgc                                          20

<210> SEQ ID NO 19
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      amyE and a 5'-portion designed from the nucleotide sequence of
      5'-flanking region of Bacillus subtilis gene, spoVG

<400> SEQUENCE: 19
tcccagaatc actttctta atcatcgctc atccatgtcg                      40

<210> SEQ ID NO 20
<211> LENGTH: 41
<212> TYPE: DNA
<213> ORGANISM: Artificial sequence
<220> FEATURE:
<223> OTHER INFORMATION: Oligonucleotide as PCR primer with a
      3'-portion designed from the nucleotide sequence of Bacillus
      subtilis gene, amyE and a 5'-portion designed from the nucleotide
      sequence of chloramphenicol resistant gene

<400> SEQUENCE: 20
gactggcttt tataatatga ggtttaggct gggcggtgat a                   41

<210> SEQ ID NO 21
<211> LENGTH: 18
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 21
tcaatgggga agagaaacc                                            18

<210> SEQ ID NO 22
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 22
tcaaaacctc tttactgccg                                           20

<210> SEQ ID NO 23
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 23
cacgtaatca aagccaggct                                           20

<210> SEQ ID NO 24
<211> LENGTH: 17
<212> TYPE: DNA
<213> ORGANISM: Artificial sequence
<220> FEATURE:
<223> OTHER INFORMATION: Oligonucleotide as the forward PCR primer used
      for the amplification of spectinomycin resistant gene from pDG1727

<400> SEQUENCE: 24
atcgattttc gttcgtg                                                      17

<210> SEQ ID NO 25
<211> LENGTH: 19
<212> TYPE: DNA
<213> ORGANISM: Artificial sequence
<220> FEATURE:
<223> OTHER INFORMATION: Oligonucleotide as the reverse PCR primer used
      for the amplification of spectinomycin resistant gene from pDG1727

<400> SEQUENCE: 25
catatgcaag ggtttattg                                                    19

<210> SEQ ID NO 26
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, sigF

<400> SEQUENCE: 26
gaagaaagcc gggtttatca                                                   20

<210> SEQ ID NO 27
<211> LENGTH: 37
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 5'-flanking region of
      Bacillus subtilis gene, sigF and a 5'-portion designed
      from the nucleotide sequence of plasmid pDG1727

<400> SEQUENCE: 27
cacgaacgaa aatcgatctg agcgtttttg ccgtttt                                37

<210> SEQ ID NO 28
<211> LENGTH: 39
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 3'-flanking region of
      Bacillus subtilis gene, sigF and a 5'-portion designed
      from the nucleotide sequence of plasmid pDG1727

<400> SEQUENCE: 28
caataaaccc ttgcatatgt ctgcagtgca ggctagctt                              39

<210> SEQ ID NO 29
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of Bacillus subtilis
      gene, sigF

<400> SEQUENCE: 29
cccgacgaac aaacctgcca                                                   20

<210> SEQ ID NO 30
<211> LENGTH: 20
<212> TYPE: DNA

```
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, sigF

<400> SEQUENCE: 30
cgaatgacca ctagttttgt                                                   20

<210> SEQ ID NO 31
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of Bacillus subtilis
      gene, sigF

<400> SEQUENCE: 31
tgaagcgtct cccatccccc                                                   20

<210> SEQ ID NO 32
<211> LENGTH: 21
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, sigE

<400> SEQUENCE: 32
agtcagatgt gaaaatctat t                                                 21

<210> SEQ ID NO 33
<211> LENGTH: 37
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 5'-flanking region of
      Bacillus subtilis gene, sigE and a 5'-portion designed
      from the nucleotide sequence of plasmid pDG1727

<400> SEQUENCE: 33
cacgaacgaa aatcgatctt cctctcccctt ctaaatg                               37

<210> SEQ ID NO 34
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 3'-flanking region of
      Bacillus subtilis gene, sigE and a 5'-portion designed
      from the nucleotide sequence of plasmid pDG1727

<400> SEQUENCE: 34
caataaaccc ttgcatatga aaattttatg gttagaaccc                             40

<210> SEQ ID NO 35
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of Bacillus
      subtilis gene, sigE

<400> SEQUENCE: 35
```
ccttactttt tccaaaacgt                                        20

<210> SEQ ID NO 36
<211> LENGTH: 21
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, sigE

<400> SEQUENCE: 36
ctcacggcat ttattttaaa a                                      21

<210> SEQ ID NO 37
<211> LENGTH: 22
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of Bacillus
      subtilis gene, sigE

<400> SEQUENCE: 37
gcttttcatt attgatgaat at                                     22

<210> SEQ ID NO 38
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus
      subtilis gene, phrA

<400> SEQUENCE: 38
agaagaccaa gatttgctgc                                        20

<210> SEQ ID NO 39
<211> LENGTH: 37
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 5'-flanking region of
      Bacillus subtilis gene, phrA and a 5'-portion designed
      from the nucleotide sequence of plasmid pDG1727

<400> SEQUENCE: 39
cacgaacgaa aatcgatatg aaatgttttc ccttctg                     37

<210> SEQ ID NO 40
<211> LENGTH: 37
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 3'-flanking
      region of Bacillus subtilis gene, phrA and a
      5'-portion designed from the nucleotide sequence of
      plasmid pDG1727

<400> SEQUENCE: 40
caataaaccc ttgcatatgg gttcatgcag gtgaaac                     37

<210> SEQ ID NO 41
<211> LENGTH: 20
<212> TYPE: DNA
<213> ORGANISM: Artificial sequence

```
<220> FEATURE:
<223> OTHER INFORMATION: Oligonucleotide as PCR primer designed from the
      nucleotide sequence of 3'-flanking region of Bacillus
      subtilis gene, phrA

<400> SEQUENCE: 41
actggccccg tgtgatgcgg                                                    20

<210> SEQ ID NO 42
<211> LENGTH: 21
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus
      subtilis gene, phrA

<400> SEQUENCE: 42
gagttttcag aattgttaga a                                                  21

<210> SEQ ID NO 43
<211> LENGTH: 19
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of Bacillus
      subtilis gene, phrA

<400> SEQUENCE: 43
gaagagactg cagcttttt                                                     19

<210> SEQ ID NO 44
<211> LENGTH: 46
<212> TYPE: DNA
<213> ORGANISM: Artificial sequence
<220> FEATURE:
<223> OTHER INFORMATION: Oligonucleotide as PCR primer designed from the
      nucleotide sequence of Bacillus clausii KSM-K16
      alkaline protease gene and the nucleotide sequence of
      Bacillus sp. KSM-S237 alkaline cellulase gene

<400> SEQUENCE: 44
actttaaaaa tatttaggag gtaatatgaa gaaaccgttg gggaaa                       46

<210> SEQ ID NO 45
<211> LENGTH: 32
<212> TYPE: DNA
<213> ORGANISM: Artificial sequence
<220> FEATURE:
<223> OTHER INFORMATION: Oligonucleotide as PCR primer designed from the
      nucleotide sequence of downstream region of Bacillus
      clausii KSM-K16 alkaline protease gene

<400> SEQUENCE: 45
gggagatctt cagcgatcta tttctctttt tc                                      32

<210> SEQ ID NO 46
<211> LENGTH: 25
<212> TYPE: DNA
<213> ORGANISM: Artificial sequence
<220> FEATURE:
<223> OTHER INFORMATION: Oligonucleotide as PCR primer designed from the
      nucleotide sequence of upstream region of Bacillus sp.
      KSM-S237 alkaline cellulase gene

<400> SEQUENCE: 46
cccggatcca acaggcttat attta                                              25
```

<210> SEQ ID NO 47
<211> LENGTH: 46
<212> TYPE: DNA
<213> ORGANISM: Artificial sequence
<220> FEATURE:
<223> OTHER INFORMATION: Oligonucleotide as PCR primer designed from the
      nucleotide sequence of Bacillus sp. KSM-S237 alkaline
      cellulase gene and the nucleotide sequence of Bacillus
      clausii KSM-K16 alkaline protease gene

<400> SEQUENCE: 47
tttccccaac ggtttcttca tattacctcc taaatatttt taaagt                46

<210> SEQ ID NO 48
<211> LENGTH: 37
<212> TYPE: DNA
<213> ORGANISM: Artificial sequence
<220> FEATURE:
<223> OTHER INFORMATION: Oligonucleotide as PCR primer designed from
      nucleotide sequence of the upstream region of the alkaline
      cellulase gene in Bacillus sp. KSM-S237 with a
      insertion of the BamHI restriction site at the 5'-end

<400> SEQUENCE: 48
ttgcggatcc aacaggctta tatttagagg aaatttc                          37

<210> SEQ ID NO 49
<211> LENGTH: 36
<212> TYPE: DNA
<213> ORGANISM: Artificial sequence
<220> FEATURE:
<223> OTHER INFORMATION: Oligonucleotide as PCR primer designed from
      nucleotide sequence of the downstream region of the alkaline
      cellulase gene in Bacillus sp. KSM-S237 with a
      insertion of the BamHI restriction site at the 5'-end

<400> SEQUENCE: 49
ttgcggatcc aacaactctg tgtccagtta tgcaag                           36

<210> SEQ ID NO 50
<211> LENGTH: 25
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus
      subtilis gene, rsiX

<400> SEQUENCE: 50
attccagtta ctcgtaatat agttg                                       25

<210> SEQ ID NO 51
<211> LENGTH: 39
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of 5'-flanking
      region of Bacillus subtilis gene, rsiX and a
      5'-portion designed from the nucleotide sequence of
      plasmid pC194

<400> SEQUENCE: 51
ctaatgggtg ctttagttga cttcatcatc cattagctc                        39

<210> SEQ ID NO 52
<211> LENGTH: 38
<212> TYPE: DNA
<213> ORGANISM: Artificial sequence

```
<220> FEATURE:
<223> OTHER INFORMATION: Oligonucleotide as PCR primer with a 3'-portion
      designed from the nucleotide sequence of 3'-flanking
      region of Bacillus subtilis gene, rsiX and a
      5'-portion designed from the nucleotide sequence of
      plasmid pC194

<400> SEQUENCE: 52
ctgccccgtt agttgaagct gctccaaatc cgatttcc                                 38

<210> SEQ ID NO 53
<211> LENGTH: 23
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of Bacillus
      subtilis gene, rsiX

<400> SEQUENCE: 53
gtcctgcatt tttcgaagtc tgg                                                 23

<210> SEQ ID NO 54
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus
      subtilis gene, rsiX

<400> SEQUENCE: 54
actccgggtc tggcataccg                                                     20

<210> SEQ ID NO 55
<211> LENGTH: 21
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of
      Bacillus subtilis gene, rsiX

<400> SEQUENCE: 55
acatctggaa gataaaattg t                                                   21

<210> SEQ ID NO 56
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of
      Bacillus subtilis gene, yacP

<400> SEQUENCE: 56
caggctgaga tcctattttt                                                     20

<210> SEQ ID NO 57
<211> LENGTH: 39
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      5'-flanking region of Bacillus subtilis gene, yacP
      and a 5'-portion designed from the nucleotide
      sequence of plasmid pC194

<400> SEQUENCE: 57
```

```
ctaatgggtg ctttagttgg ggtctttatt ctcccacag                              39

<210> SEQ ID NO 58
<211> LENGTH: 38
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      3'-flanking region of Bacillus subtilis gene, yacP
      and a 5'-portion designed from the nucleotide
      sequence of plasmid pC194

<400> SEQUENCE: 58
ctgccccgtt agttgaaggt tgacgctttt ttgcccaa                               38

<210> SEQ ID NO 59
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of
      Bacillus subtilis gene, yacP

<400> SEQUENCE: 59
acgcatgtaa aagacctcca                                                  20

<210> SEQ ID NO 60
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of
      Bacillus subtilis gene, yacP

<400> SEQUENCE: 60
gaggcagaaa tgccaagtca                                                  20

<210> SEQ ID NO 61
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 3'-flanking region of
      Bacillus subtilis gene, yacP

<400> SEQUENCE: 61
ttgcaagtac tgcagtattt                                                  20

<210> SEQ ID NO 62
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of
      Bacillus subtilis gene, yvdE

<400> SEQUENCE: 62
cttcctccat taaaaagccg                                                  20

<210> SEQ ID NO 63
<211> LENGTH: 39
<212> TYPE: DNA
<213> ORGANISM: Artificial sequence
```

```
<220> FEATURE:
<223> OTHER INFORMATION: Oligonucleotide as PCR primer with a 3'-portion
      designed from the nucleotide sequence of
      5'-flanking region of Bacillus subtilis gene,
      yvdE and a 5'-portion designed from the
      nucleotide sequence of plasmid pC194

<400> SEQUENCE: 63
ctaatgggtg ctttagttgt ttcatcccct ccttatctg                                39

<210> SEQ ID NO 64
<211> LENGTH: 38
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      3'-flanking region of Bacillus subtilis gene,
      yvdE and a 5'-portion designed from the
      nucleotide sequence of plasmid pC194

<400> SEQUENCE: 64
ctgccccgtt agttgaaggc gccttattct gttatcgg                                 38

<210> SEQ ID NO 65
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, yvdE

<400> SEQUENCE: 65
cggcatatca gctgtaaaag                                                     20

<210> SEQ ID NO 66
<211> LENGTH: 21
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region
      of Bacillus subtilis gene, yvdE

<400> SEQUENCE: 66
tttcatccat ttttctgcat c                                                   21

<210> SEQ ID NO 67
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, yvdE

<400> SEQUENCE: 67
cagtccttat agcgggattg                                                     20

<210> SEQ ID NO 68
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of
      Bacillus subtilis gene, yurK

<400> SEQUENCE: 68
```
cttcagccgc tttgctttt    20

<210> SEQ ID NO 69
<211> LENGTH: 39
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      5'-flanking region of Bacillus subtilis gene,
      yurK and a 5'-portion designed from the
      nucleotide sequence of plasmid pC194

<400> SEQUENCE: 69
ctaatgggtg cttagttga gggtagcctc cttttaacc    39

<210> SEQ ID NO 70
<211> LENGTH: 38
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      3'-flanking region of Bacillus subtilis gene,
      yurK and a 5'-portion designed from the
      nucleotide sequence of plasmid pC194

<400> SEQUENCE: 70
ctgccccgtt agttgaagca ggcataaaaa acgagaca    38

<210> SEQ ID NO 71
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, yurK

<400> SEQUENCE: 71
gtcctgctgg cggggttaac    20

<210> SEQ ID NO 72
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region
      of Bacillus subtilis gene, yurK

<400> SEQUENCE: 72
tgctgctgtt ctatgatgcc    20

<210> SEQ ID NO 73
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, yurK

<400> SEQUENCE: 73
ttgtccgcgg gattgcaagc    20

<210> SEQ ID NO 74
<211> LENGTH: 20

```
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region
      of Bacillus subtilis gene, yhdQ

<400> SEQUENCE: 74
tcacaaatcc aagcgttcga                                                    20

<210> SEQ ID NO 75
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      5'-flanking region of Bacillus subtilis gene,
      yhdQ and a 5'-portion designed from the
      nucleotide sequence of plasmid pC194

<400> SEQUENCE: 75
ctaatgggtg ctttagttgc acgttatagt tatgagaata                              40

<210> SEQ ID NO 76
<211> LENGTH: 39
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of
      3'-flanking region of Bacillus subtilis gene,
      yhdQ and a 5'-portion designed from the
      nucleotide sequence of plasmid pC194

<400> SEQUENCE: 76
ctgccccgtt agttgaagaa ccattttatc taacaggag                               39

<210> SEQ ID NO 77
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, yhdQ

<400> SEQUENCE: 77
tgtggaccct ctcttttgc                                                     20

<210> SEQ ID NO 78
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region
      of Bacillus subtilis gene, yhdQ

<400> SEQUENCE: 78
gtccaatccg atatacccga                                                    20

<210> SEQ ID NO 79
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, yhdQ
```

```
<400> SEQUENCE: 79
agggttgacg aattgagaaa                                              20

<210> SEQ ID NO 80
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking region
      of Bacillus subtilis gene, glcT

<400> SEQUENCE: 80
aagccggtgt ctctgttaca                                              20

<210> SEQ ID NO 81
<211> LENGTH: 39
<212> TYPE: DNA
<213> ORGANISM: Artificial sequence
<220> FEATURE:
<223> OTHER INFORMATION: Oligonucleotide as PCR primer with a
      3'-portion designed from the nucleotide
      sequence of 5'-flanking region of Bacillus
      subtilis gene, glcT and a 5'-portion designed
      from the nucleotide sequence of plasmid pC194

<400> SEQUENCE: 81
ctaatgggtg ctttagttgt caatacctca tatcgtaca                         39

<210> SEQ ID NO 82
<211> LENGTH: 41
<212> TYPE: DNA
<213> ORGANISM: Artificial sequence
<220> FEATURE:
<223> OTHER INFORMATION: Oligonucleotide as PCR primer with a
      3'-portion designed from the nucleotide
      sequence of 3'-flanking region of Bacillus
      subtilis gene, glcT and a 5'-portion designed
      from the nucleotide sequence of plasmid pC194

<400> SEQUENCE: 82
ctgccccgtt agttgaagaa tttcataaat tcagtttatc c                      41

<210> SEQ ID NO 83
<211> LENGTH: 21
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking region
      of Bacillus subtilis gene, glcT

<400> SEQUENCE: 83
cttatagctg aagaattcat a                                            21

<210> SEQ ID NO 84
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 5'-flanking
      region of Bacillus subtilis gene, glcT

<400> SEQUENCE: 84
aaaaagagtg tttgaggcaa                                              20
```

```
<210> SEQ ID NO 85
<211> LENGTH: 20
<212> TYPE: DNA
<213> ORGANISM: Artificial sequence
<220> FEATURE:
<223> OTHER INFORMATION: Oligonucleotide as PCR primer designed from
      the nucleotide sequence of 3'-flanking
      region of Bacillus subtilis gene, glcT

<400> SEQUENCE: 85
gttcaatcac cccgaagata                                              20
```

RECOMBINANT MICROORGANISM THAT EXPRESSES A *SECY* GENE WITH DELETION OF SPORULATION-ASSOCIATED GENES AND METHOD OF PRODUCING THEREOF

REFERENCE TO SEQUENCE LISTING SUBMITTED ELECTRONICALLY

The content of the electronically submitted substitute sequence listing, file name: SequenceListing.TXT; Size: 83,968 bytes; and Date of Creation: Sep. 4, 2009, filed herewith, is incorporated herein by reference in its entirety.

FIELD OF THE INVENTION

The present invention relates to a recombinant microorganism used in the production of a useful protein or polypeptide, and a method for producing the protein or polypeptide.

BACKGROUND OF THE INVENTION

Industrial production of useful materials by use of microorganisms is carried out for an extensive range of materials, the types including foodstuffs such as alcoholic beverages, soybean paste and soybean sauce, as well as amino acids, organic acids, nucleic acid-related substances, antibiotic substances, carbohydrates, lipids, proteins, and the like. Applications of these substances are also being expanded over a broad range of fields, including foods, pharmaceuticals, detergents, products for daily use such as cosmetics, and a variety of chemical raw materials.

With regard to such industrial production of useful materials by microorganisms, one important challenge is to improve productivity, and as a measure therefor, breeding of productive microorganisms through genetic techniques such as mutation has been conducted. Recently, in particular, advances in microbial genetics and biotechnology have allowed more efficient breeding of productive microorganisms using genetic recombination technology and the like. In addition, the rapid advancement of genome analysis technology in recent years has resulted in attempts to interpret the genomic data of microorganisms of interest and industrially utilize the obtained information more actively. Examples of industrially useful host microorganisms whose genomic data have been disclosed include *Bacillus subtilis* Marburg No. 168 (Non-Patent Document 1), *Escherichia coli* K-12 MG1655 (Non-Patent Document 2), *Corynebacterium glutamicum* ATCC132032, and the like, and further improved microbial strains have been developed using these genomic data. However, regardless of such efforts, the production efficiencies are not necessarily satisfactory.

For certain types of microorganisms, strains in which a gene associated with the early stage of sporulation has been deleted or inactivated, have been recently constructed, and thereby an effect of improving the productivity for proteins or polypeptides is being obtained. For example, it has been reported that the productivity for the secretion of cellulase and the like is increased by using a host strain in which sigE gene, sigF gene, spoIIE gene, spoIISB gene or sigG gene of *Bacillus subtilis*, or a group of genes included in a region extending from spoIVCB gene to spoIIIC gene, has been deleted (Patent Document 1).

Furthermore, the functions for operating the protein translocation system (Sec route) in *Bacillus subtilis* are shared by SecA which serves as a motor for expelling secreted proteins to the outside of cells, and the three proteins, SecY, SecE and SecG, constituting the main part of the translocation channel through which the secreted proteins pass, as well as SecDF which is a co-factor for the translocation channel, and the like. Inter alia, there have been reports on an expression vector capable of overexpressing secG gene, which encodes SecG protein (Patent Document 2), or a Gram-positive bacterium in which expression of secG gene has been changed by altering the ribosome binding site of SecG gene (Patent Document 3). Thus, it is shown that the breeding of a *Bacillus subtilis* species having SecG gene destroyed is inhibited during the production of heterologous proteins. It is also reported that in *Escherichia coli*, variation in secY gene inhibits the breeding at low temperatures or the secretion of proteins (Non-Patent Document 3).

However, a microorganism which overexpresses secY gene, and also has a sporulation-associated gene deleted or inactivated, is not known hitherto.
[Patent Document 1] JP-A-2003-47490
[Patent Document 2] JP-A-2001-510046
[Patent Document 3] US-A-2003/0157642
[Non-Patent Document 1] Nature, 390, 249, 1997
[Non-Patent Document 2] Science, 277, 1453, 1997
[Non-Patent Document 3] Cell, 32, 789, 1983.

DISCLOSURE OF THE INVENTION

The present invention has the following aspects.

(1) A recombinant microorganism obtained by transfecting a gene encoding a desired protein or polypeptide into a microorganism strain which is obtained by genetically constructing to overexpress secY gene of *Bacillus subtilis* or a gene corresponding to the secY gene, and deleting or inactivating one or more genes selected from sporulation-associated genes and genes corresponding to the sporulation-associated genes from the genome.

(2) A method of producing a recombinant microorganism as set forth in claim 1, which includes, in a microorganism, introducing a transcription initiation control region or a transcription initiation control region and ribosome binding site, having a function in a microorganism, to the upstream on the genome of secY gene of *Bacillus subtilis* or a gene corresponding to the secY gene, or to the upstream of the leader gene of an operon on the genome containing secY gene of *Bacillus subtilis* or a corresponding gene, or obtained by introducing a gene fragment in which a transcription initiation control region or a transcription initiation control region and ribosome binding site, having a function in a microorganism, is linked to the upstream of secY gene of *Bacillus subtilis* or a gene corresponding to the secY gene;

deleting or inactivating one or more genes selected from sporulation-associated genes and genes corresponding to the sporulation-associated genes; and transfecting a gene encoding a desired protein or polypeptide into a microorganism strain.

(3) A method for producing a desired protein or polypeptide using the recombinant microorganism.

BEST MODE FOR CARRYING OUT THE INVENTION

Figure 1:
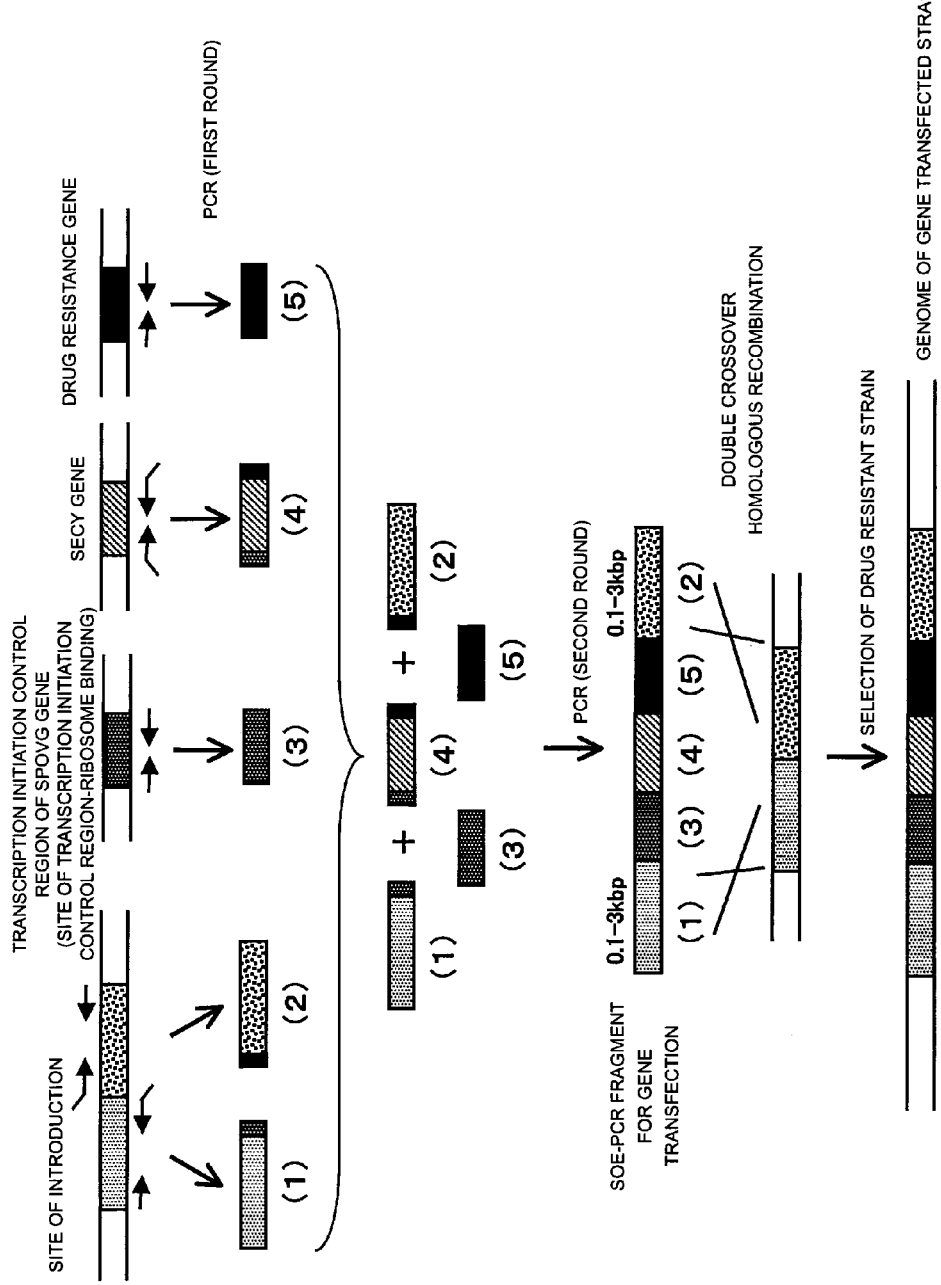
FIG. 1 is a schematic diagram showing gene transfection using a bound nucleic acid fragment prepared by SOE-PCR method.

The present invention relates to a microorganism having improved productivity for a protein or polypeptide, and a method for producing a desired protein or polypeptide using the microorganism.

The inventors of the present invention have searched for a gene which affects the production of a useful protein or polypeptide among a variety of genes encoded on the genome of microorganism, and found that when a gene encoding a desired protein or polypeptide is transfected into a microorganism strain in which secY gene of *Bacillus subtilis* has been enhanced to overexpress SecY of *Bacillus subtilis*, as well as sporulation-associated genes are regulated, the productivity for the desired protein or polypeptide is improved compared to the productivity before the alteration.

The recombinant microorganism of the present invention is a microorganism having high productivity for a desired protein or a desired polypeptide. Therefore, when production of a desired protein or a desired polypeptide is performed using this recombinant microorganism, the time or costs required for the production of the material can be reduced.

The identity of amino acid sequences and base sequences in the present invention is calculated by the Lipman-Pearson method (Science, 227, 1435 (1985)). Specifically, the identity is calculated by performing an analysis using a homology analysis program (Search Homology) of genetic data processing software, Genetyx-Win (Software Development Co., Ltd.), with the unit size to compare (ktup) being set to 2.

In the present specification, the transcription initiation control region is a region including a promoter and a transcription initiation point, and the ribosome binding site is a site corresponding to the Shine-Dalgarno (SD) sequence which forms a translation initiation control region together with an initiation codon (Proc. Natl. Acad. Sci. USA, 71, 1342 (1974)).

According to the present invention, the terms upstream and downstream of a gene refer not to the locations with respect to the replication initiation point, but the upstream indicates a region following the 5'-end of a gene or region of interest, while the downstream indicates a region following the 3'-end of a gene or region of interest.

Parent microorganisms for constructing the microorganism of the present invention may be any microorganisms having secY gene of *Bacillus subtilis* or a gene corresponding thereto, and these may be wild-type microorganisms as well as mutated microorganisms. Specifically, bacteria of the genus *Bacillus*, bacteria of the genus *Clostridium*, yeast or the like may be mentioned, and among them, bacteria of the genus *Bacillus* are preferred. Furthermore, *Bacillus subtilis* is even more preferred from the viewpoints that the entire genomic information for the microorganism has been revealed, and thus relevant technologies of genetic engineering and genomic engineering are constructed, and that the microorganism has an ability to secrete and produce a protein outside the bacterial cell.

The names of various genes and gene regions of *Bacillus subtilis* described the present specification are described on the basis of the *Bacillus subtilis* genome data reported in Nature, 390, 249-256 (1997), and published in the Internet on the website of JAFAN: Japan Functional Analysis Network for *Bacillus subtilis* (BSORF DB) (bacillus.genome.ad.jp/, renewed on Mar. 10, 2004).

The secY gene of *Bacillus subtilis* of the present invention refers to a gene having the base sequence set forth in SEQ ID NO: 1. The gene corresponding to secY gene of *Bacillus subtilis* refers to a gene having the substantially same function as that of the secY gene of *Bacillus subtilis*, and for example, the respective secY genes identified mainly by genome analysis and genes encoding SecY protein in *Bacillus licheniformis, Bacillus anthracis, Bacillus cereus, Bacillus thuringiensis, OceanoBacillus iheyensis* and the like, may be mentioned. Furthermore, there are cases where two kinds of the corresponding gene are identified in a microorganism, such as in *Bacillus anthracis*. As the genes corresponding to the secY gene of *Bacillus subtilis*, any of the following genes of (1) to (4) may be mentioned.

(1) A gene comprising a DNA which has a base sequence having at least 90%, preferably at least 95%, and more preferably at least 99%, identity to the base sequence set forth in SEQ ID NO: 1, and encodes a protein which is functionally equivalent to a protein having the amino acid sequence set forth in SEQ ID NO: 2.

(2) A gene comprising a DNA which is hybridized with a DNA comprising a base sequence complementary to the base sequence set forth in SEQ ID NO: 1 under stringent conditions, and encodes a protein which is functionally equivalent to a protein having the amino acid sequence set forth in SEQ ID NO: 2.

Additionally, as for the "stringent conditions" as used herein, there may be mentioned, for example, the method described in Molecular Cloning—A LABORATORY MANUAL THIRD EDITION [Joseph Sambrook, David W. Russell, Cold Spring Harbor Laboratory Press], and for example, conditions for hybridizing by thermostatically maintaining at 65° C. for 8 to 16 hours, together with a probe in a solution containing 6×SSC (composition of 1×SSC: 0.15 M sodium chloride, 0.015 M sodium citrate, pH 7.0), 0.5% SDS, 5×Denhardts and 1.00 mg/mL of herring sperm DNA, may be mentioned.

(3) A gene comprising a DNA which has an amino acid sequence having at least 90%, preferably at least 95%, and more preferably at least 99%, identity to the amino acid sequence set forth in SEQ ID NO: 2, and encodes a protein which is functionally equivalent to a protein having the amino acid sequence set forth in SEQ ID NO: 2.

(4) A gene comprising a DNA which has an amino acid sequence having one or two or more amino acids deleted, substituted or added in the amino acid sequence set forth in SEQ ID NO: 2, and encodes a protein which is functionally equivalent to a protein having the amino acid sequence set forth in SEQ ID NO: 2.

Additionally, the amino acid sequence having one or two or more amino acids deleted, substituted or added in the amino acid sequence set forth in SEQ ID NO: 2 as used herein includes amino acid sequences having one or several, preferably 1 to 10, amino acids deleted, substituted or added, and the addition includes addition of one to several amino acids to both terminals of an amino acid sequence.

In addition, the protein which is functionally equivalent to a protein having the amino acid sequence set forth in SEQ ID NO: 2 refers to a protein which has the substantially same function as that of a protein encoded by secY gene, and is capable of constituting an important part of a translocation channel through which secreted proteins pass.

The term overexpression of secY gene of *Bacillus subtilis* or a gene corresponding to the secY gene indicates that expression in a host of secY gene of *Bacillus subtilis* or a gene corresponding to the secY gene in an amount exceeding the usual amount of expression is observed. Examples of the means for overexpressing the secY gene of *Bacillus subtilis* or the gene corresponding to the secY gene include introduction of a transcription initiation control region or a site of transcription initiation control region and ribosome binding site, having a function in a microorganism, to the upstream of the secY gene of *Bacillus subtilis* or the gene corresponding to the secY gene in the genome or to the upstream of the leader gene of an operon on the genome containing secY gene of *Bacillus subtilis* or a gene corresponding to the secY gene, or introduction of a gene fragment in which a transcription initiation control region or a transcription initiation control region and ribosome binding site, having a function in a microorganism, is linked to the upstream of the secY gene of *Bacillus subtilis* or a gene corresponding to the secY gene.

Here, the transcription initiation control region or the transcription initiation control region and ribosome binding site, having a function in a microorganism, is not particularly limited as long as the region is a transcription initiation control region or a transcription initiation control region and ribosome binding site, having a function in the microorganism which serves as a host, for example, a transcription initiation control region or a transcription initiation control region and ribosome binding site located upstream to spoVG gene or aprE gene of *Bacillus subtilis*, or a gene corresponding to any of these genes, is preferred, and a transcription initiation control region or a transcription initiation control region and ribosome binding site located upstream to spoVG gene of *Bacillus subtilis*, or a gene corresponding to the spoVG gene is more preferred.

As the transcription initiation control region of the spoVG gene of *Bacillus subtilis*, there may be mentioned a region for controlling the transcription of spoVG gene, which is a gene disclosed as Gene No. BG10112 in the Internet website (bacillus.genome.ad.jp/, renewed on Mar. 10, 2004) by JAFAN: Japan Functional Analysis Network for *Bacillus subtilis* (BSORF DB). More specifically, a DNA having a base sequence from base No. 38 to base No. 210 of the base sequence set forth in SEQ ID NO: 9, or a DNA comprising a base sequence homologous to the aforementioned base sequence and having a function as the transcription initiation control region of spoVG gene of *Bacillus subtilis*, may be mentioned. Furthermore, as the transcription initiation control region and ribosome binding site of spoVG gene of *Bacillus subtilis*, there may be mentioned a DNA comprising a base sequence from base No. 38 to base No. 230 of the base sequence set forth in SEQ ID NO: 9, or a DNA comprising a base sequence homologous to the aforementioned base sequence and having a function as the transcription initiation control region and ribosome binding site of spoVG gene of *Bacillus subtilis*.

Examples of the base sequence homologous to the base sequence from base No. 38 to base No. 210 or the base sequence from base No. 38 to base No. 230 of the base sequence set forth in SEQ ID NO: 9, include (A) a base sequence comprising a DNA which is hybridized with a DNA comprising a base sequence complementary to the base sequence from base No. 38 to base No. 210 or from base No. 38 to base No. 230 of the base sequence set forth in SEQ ID NO: 9, under stringent conditions; (B) a base sequence having at least 90%, preferably at least 95%, and more preferably at least 99%, identity to the base sequence from base No. 38 to base No. 210 or from base No. 38 to base No. 230 of the base sequence set forth in SEQ ID NO: 9; and the like.

Additionally, the term "stringent conditions" as used herein may be exemplified by the same conditions as described above.

The phrase "having a function as the transcription initiation control region of spoVG gene of *Bacillus subtilis*, or as the transcription initiation control region and ribosome binding site" implies that when the DNA having the function is introduced to the upstream of secY gene of *Bacillus subtilis* or a gene corresponding to the secY gene, or to the upstream of the leader gene of an operon (rpsJ gene for *Bacillus subtilis*) on the genome containing secY gene of *Bacillus subtilis* or a corresponding gene, the secY gene or the gene corresponding to the secY gene is overexpressed, thereby resulting in an improvement of the productivity for a desired protein or polypeptide, and also the extent of improvement is equal to the improvement obtained in the case where the transcription initiation control region of spoVG gene of *Bacillus subtilis* or the transcription initiation control region and ribosome binding site is introduced to the upstream of the secY gene of *Bacillus subtilis* or a gene corresponding to the secY gene, or to the upstream of the leader gene of an operon (rpsJ gene for *Bacillus subtilis*) on the genome containing secY gene of *Bacillus subtilis* or a corresponding gene.

The introduction of the transcription initiation control region or the transcription initiation control region and ribosome binding site, to the upstream of the secY gene or a gene corresponding to the secY gene on the genome, or to the upstream of the leader gene of an operon (rpsJ gene for *Bacillus subtilis*) on the genome containing secY gene of *Bacillus subtilis* or a corresponding gene, includes partial or entire substitution of the original transcription initiation control region of the secY gene of *Bacillus subtilis* or a gene corresponding to the secY gene, or of an operon on the genome containing secY gene of *Bacillus subtilis* or a corresponding gene, as well as insertion while retaining the original transcription initiation control region or the transcription initiation control region and ribosome binding site.

The substitution of the transcription initiation control region or the transcription initiation control region and ribosome binding site can be performed, for example, using a known method involving homologous recombination. That is, first, to the upstream of a DNA fragment containing such transcription initiation control region or the transcription initiation control region and ribosome binding site, a DNA fragment containing the upstream region of the original transcription initiation control region of an operon containing secY gene, and a drug resistance gene fragment are linked, while to the downstream of the former DNA fragment, a DNA fragment containing a part or the entirety of the translation initiation control region and the structural gene region of rpsJ gene, which is the leader gene of an operon containing secY gene, or a part or the entirety of the structural gene region of rpsJ gene, is linked, by a known method such as the SOE (splicing by overlap extension)-PCR method (Gene, 77, 61, 1989). In this manner, a DNA fragment is obtained, in which the DNA fragment containing the upstream region of the original transcription initiation control region of an operon containing secY gene, a drug resistance gene fragment, a DNA fragment containing the subject transcription initiation control region or the subject site of ribosome biding to the transcription initiation control region, and a DNA fragment containing a part or the entirety of the translation initiation control region and the structural gene region of rpsJ gene, or a part or the entirety of the structural gene region of rpsJ gene, are linked in this order.

Next, when such DNA fragment is transfected into the cells of a parent microorganism by a known method, double crossover homologous recombination occurs at two spots of the genome of the parent microorganism, such as the upstream region of the original transcription initiation control region of the operon containing secY gene, and the region including a part or the entirety of the translation initiation control region and the structural gene region of rpsJ gene, or a part or the entirety of the structural gene region of rpsJ gene. As a result, a transformant in which the original transcription initiation control region or the transcription initiation control region and ribosome binding site is substituted by the subject transcription initiation control region or the subject transcription initiation control region and ribosome binding site, can be isolated using the drug resistance gene as a marker. In this manner, the transcription initiation control region or the transcription initiation control region and ribosome binding site introduced to the upstream of the operon containing secY gene on the genome, may be genetically stably maintained. In addition, as the known method for transfecting a host microorganism with a DNA fragment for transfection, specifically there may be mentioned a competent cell transformation method (J. Bacteriol. 93, 1925 (1967)), a protoplast transformation method (Mol. Gen. Genet. 168, 111 (1979)), an electroporation method (FEMS Microbiol. Lett. 55, 135 (1990)), or the like, and a competent cell transformation method in particular is preferred.

In particular, in the case of using *Bacillus subtilis* as the host microorganism of the present invention, the substitution through homologous recombination from the original transcription initiation control region of the operon containing secY gene or the transcription initiation control region and ribosome binding site, to the subject transcription initiation control region or the subject transcription initiation control region and ribosome binding site, can be performed using the method described in Mol. Gen. Genet., 223, 268 (1990) or the like.

The insertion of the subject transcription initiation control region or the subject transcription initiation control region and ribosome binding site can be performed by the same method as the aforementioned method of substitution, if the sequences of the DNA fragments to be added to the two terminals of the transcription initiation control region or the transcription initiation control region and ribosome binding site desired for insertion, are appropriately selected. For example, to the upstream of such transcription initiation control region, a DNA fragment containing the upstream region of the original transcription initiation control region of an operon containing secY gene, and a drug resistance gene fragment are linked, while to the downstream of such transcription initiation control region, a DNA fragment containing a part or the entirety of the original transcription initiation control region is linked. In this manner, there is obtained a DNA fragment in which a DNA fragment containing the upstream region of the original transcription initiation control region of an operon containing secY gene, a drug resistance gene fragment, the subject transcription initiation control region, and a DNA fragment containing a part or the entirety of the original transcription initiation control region, are linked in this order. Subsequently, such DNA fragment is inserted into a host microorganism, and then the transformant can be isolated using the drug resistance gene as a marker. On the genome of the transformant thus isolated, the original transcription initiation control region of the operon containing secY gene and the subject transcription initiation control region may be stably maintained, while being adjacent to each other without any gap therebetween. Alternatively, when a DNA fragment in which a DNA fragment containing the upstream region of secY gene and a drug resistance gene fragment are linked upstream to the subject transcription initiation control region, while a DNA fragment containing a part or the entirety of secY gene is linked downstream to the subject transcription initiation control region, is prepared and used, the subject transcription initiation control region may be maintained stably, while being introduced immediately upstream to the secY gene.

According to the present invention, the upstream on the genome to which a transcription initiation control region or a transcription initiation control region and ribosome binding site, having a function in a microorganism, is introduced includes secY gene. The upstream is not particularly limited if the region is the upstream side of the initiation codon of rpsJ gene which is the operon leader gene, or the upstream side of the initiation codon of secY gene, but a region including 2000 adjacent base pairs is preferred, a region including 500 base pairs is more preferred, a region including 100 base pairs is even more preferred, and a region including 50 base pairs is even more preferred.

According to the present invention, the introduction of a gene fragment in which the subject transcription initiation control region or the transcription initiation control region and ribosome binding site is linked upstream to secY gene or a gene corresponding to the secY gene, can be performed using a gene fragment obtained by linking a fragment of the subject transcription initiation control region or the transcription initiation control region and ribosome binding site, to a fragment of the secY gene or a gene corresponding to the secY gene, which fragments have been obtained by a known cloning method, such as a PCR method, with the genome of a microorganism other than *Bacillus subtilis* used as the template, through a known method such as a restriction enzyme method or an SOE (splicing by overlap extension)-PCR method (Gene, 77, 61 (1989)). Such fragments can be introduced to the chromosome by allowing homologous recombination between a nucleic acid fragment introduced into the cell and the chromosome, according to a known transformation method.

The base sequence of the secY gene or a gene corresponding to the secY gene to be introduced, may not coincide with the base sequence of the secY gene originally possessed by the microorganism or a gene corresponding to the secY gene, as long as it is the base sequence of secY gene or a gene corresponding to the secY gene. Furthermore, the base sequence of the transcription initiation control region or the transcription initiation control region and ribosome binding site, having a function in a microorganism, such as the transcription initiation control region or the transcription initiation control region and ribosome binding site of spoVG gene of *Bacillus subtilis* to be introduced, may not coincide with the base sequence possessed by the microorganism, as long as it is the subject base sequence. The method of introducing a nucleic acid fragment into a host may be exemplified by a competent cell transformation method, a protoplast transformation method, an electroporation method or the like, and a competent cell transformation method in particular is preferred.

Furthermore, such fragment can also be introduced into the cytoplasm by a vector such as a plasmid. Additionally, as shown in the Examples that will be described later, since such fragment exhibits sufficient effects on the production of a desired protein or polypeptide by introducing one copy per one bacterial cell, when introduced by means of a plasmid, the fragment is hardly affected even if some of the plasmids are dropped out during the production and culture.

In addition, as for the region of chromosome allowing the introduction in a host, the inner part of a non-essential gene, or the inner part of a non-gene region upstream to a non-essential gene is preferred. For example, there may be mentioned the inner parts of aprE gene, sacB gene, nprE gene, amyE gene and ybxG gene, or the inner parts of non-gene regions upstream to these genes, but the inner part of amyE gene, or the inner part of a non-gene region upstream to ybxG gene is preferred.

The term "non-essential gene" as used herein means a gene with which the host can still survive at least under certain conditions even when the gene is destroyed. Also, even if the introduction is accompanied by deletion of a non-essential gene, or of a part or the entirety of a non-gene region upstream of a non-essential gene, there is no problem resulting therefrom.

According to the present invention, overexpression of the secY gene of *Bacillus subtilis* or a gene corresponding to the secY gene, as well as overexpression of another gene associated with the Sec route of *Bacillus subtilis*, for example, secE gene or the like, may be carried out within the scope of not affecting the improvement of productivity for a desired protein or polypeptide, and inactivation or deletion of one or two or more genes may also be implemented in parallel. Additionally, the inactivation or deletion of a gene includes substitution and deletion of a part or all of the bases in the gene, as well as insertion of bases into the gene.

Hereinafter, the method of introducing a gene fragment in which the transcription initiation control region or the transcription initiation control region and ribosome binding site of spoVG gene is linked to the upstream of secY gene, to the genome of a host by means of double crossover, using a DNA fragment prepared according to the SOE (splicing by overlap extension)-PCR method (Gene, 77, 61 (1989)), will be described in more detail. However, the method of introducing according to the present invention is not intended to be limited to the following.

The DNA fragment for introduction used in the present method is a DNA fragment in which between a fragment (hereinafter, fragment (1)) of about 0.1 to 3 kb in size, preferably 0.4 to 3 kb, adjacent to the upstream of the site of introduction on the genome of the host, and a fragment (hereinafter, fragment (2)) of about 0.1 to 3 kb in size, preferably 0.4 to 3 kb, adjacent to the downstream of the site of introduction, there is inserted a fragment containing the transcription initiation control region or the transcription initiation control region and ribosome binding site of the spoVG gene (hereinafter, fragment (3)), a secY gene fragment (hereinafter, fragment (4)), and a fragment of a drug resistance marker gene such as chloramphenicol resistance gene (hereinafter, fragment (5)), in this order. First, five fragments of fragment (1) to fragment (5) are prepared in the first round of PCR. At this time, a primer designed such that, for example, a sequence of 10 to 30 base pairs on the upstream side of the fragment (3) is added to the downstream end of the fragment (1), a sequence of 10 to 30 base pairs on the downstream side of the fragment (3) is added to the upstream end of the fragment (4), a sequence of 10 to 30 base pairs on the upstream side of the fragment (5) is added to the downstream end of the fragment (4), and a sequence of 10 to 30 base pairs on the downstream side of the fragment (5) is added upstream to the fragment (2), is used (FIG. 1).

Subsequently, the five kinds of PCR fragments prepared in the first round are used as templates, and the second round of PCR is performed using the primer located upstream to the fragment (1) and the primer located downstream to the fragment (2). Thereby, annealing occurs with the fragment (3) in the sequence of the fragment (3) added to the downstream end of the fragment (1), annealing occurs with the fragment (3) in the sequence of the fragment (3) added to the upstream end of the fragment (4), annealing occurs with the fragment (5) in the sequence of the fragment (5) added to the downstream end of the fragment (4), and annealing occurs with the fragment (5) in the sequence of the fragment (5) added upstream to the fragment (2). Thus, as a result of PCR amplification, a DNA fragment in which the five fragments of fragment (1) to fragment (5) are bound in the order of (1), (3), (4), (5) and (2), can be obtained (FIG. 1).

The PCR reaction performed herein may be favorably performed under conventional conditions described in literatures (PCR Protocols. Current methods and Applications, Edited by B. A. White, Humana Press, pp. 251, 1993; Gene, 77, 61 (1989)), using the primer set indicated in Table 1 and using an enzyme kit for general PCR, such as Pyrobest DNA polymerase (Takara Shuzo Co., Ltd.).

When the DNA fragment for transfection thus obtained is transfected into cells by a competent method or the like, gene recombination occurs within the cells, in the homologous regions upstream and downstream to the site of introduction on the genome, where identity exists, and cells transfected with a gene fragment in which the transcription initiation control region or the transcription initiation control region and ribosome binding site of the spoVG gene is linked to the upstream of the secY gene, can be isolated through selection based on the drug resistance marker. The selection based on the drug resistance marker may be favorably performed by isolating colonies which grow on an agar medium containing chloramphenicol, and then selecting the cells for which introduction on the genome is confirmed by a PCR method using the genome as the template, or the like.

In addition, the drug resistance marker gene is not particularly limited as long as it can be used in the selection using a generally used antibiotic substance, but in addition to the chloramphenicol resistance gene, there may be mentioned drug resistance marker genes such as erythromycin resistance gene, neomycin resistance gene, spectinomycin, tetracycline resistance gene and blasticidin S resistance gene.

In the recombinant microorganism of the present invention, in addition to the overexpression of SecY resulting from the enhancement of secY gene, deletion or inactivation of one or more of sporulation-associated genes and genes corresponding thereto from the genome is achieved. The deletion or inactivation of the gene is an alteration to suppress sporulation, as shown in Examples 2 and 3.

According to the present invention, examples of the sporulation-associated genes include groups of genes accelerating the formation of spores, thus deletion or inactivation of each of those genes resulting in substantial inhibition of the process of sporulation, such as the group of genes encoding sigma factors specific to the stages of sporulation, or the group of genes associated with the expression of the sigma factor genes and the activation of sigma factors. Furthermore, the group of genes that are transcribed by the corresponding sigma factors, and are involved in the acceleration of sporulation, is also included.

For *Bacillus subtilis*, among the bacteria of the genus *Bacillus*, 17 sigma factors have been identified, and starting from SigA which is a major sigma factor involved in the transcription of the genes essential for growth in the nutrition growth stage (housekeeping sigma factor), SigH, SigF, SigE, SigG and SigK which are sigma factors for controlling the process of sporulation, SigD which is a sigma factor for controlling the formation of flagella or cell wall digestion, SigL which is a sigma factor for controlling the metabolism of certain types of amino acid or sugar, SigB which is a sigma factor for controlling the response to environmental changes, sigma factors called ECF sigma factors, and the like are known to exist (*Bacillus subtilis* and Its Closest Relatives:

From Genes to Cells, Edited by A. L. Sonenshein, American Society for Microbiology, pp. 289 (2002)).

Figure 2:
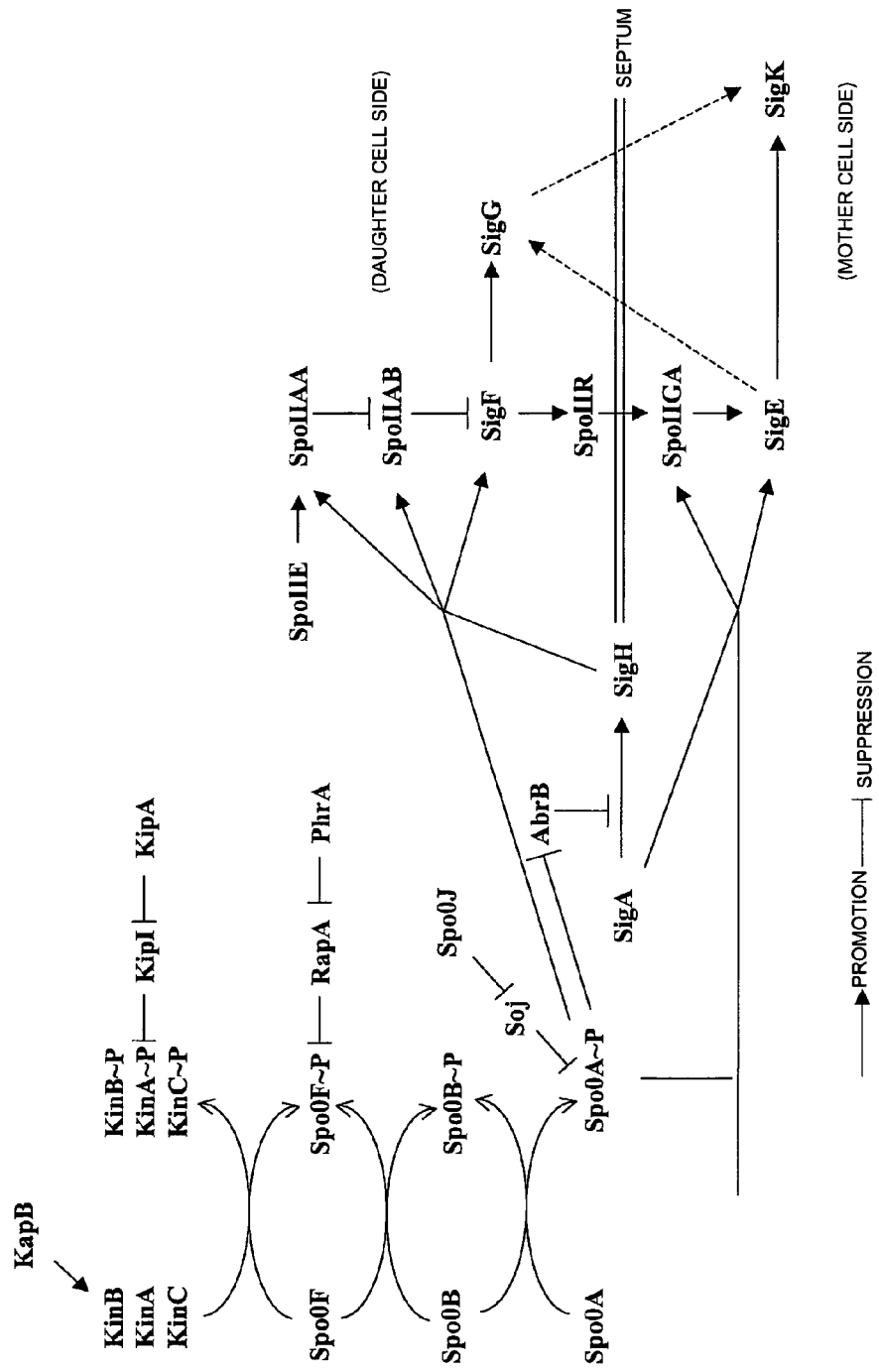
FIG. 2 is a diagram illustrating the sporulation signal transduction in *Bacillus subtilis*.

Among them, the sigma factors for controlling the process of sporulation are known to be sequentially expressed and activated according to the progress of the sporulation process, as shown in FIG. 2. In other words, when *Bacillus subtilis* enters a nutrient starvation state, there occurs first phosphorylation of Spo0A, which is a spoluration initiation control factor, via a multi-stage phosphate transduction system involving a plurality of proteins, called the phosphate relay system (Cell, 64, 545 (1991)). More specifically, auto-phosphorylation of KinA present in the cytoplasm, and of KinB and KinC present in the cell membrane, occurs as a result of nutrient starvation, and the phosphoryl group is transferred to Spo0A via Spo0F and Spo0B, thereby phosphorylated Spo0A (Phosphorylated Spo0A) being produced. Furthermore, KapB is required in the activation of the process of sporulation involving KinB (Mol. Microbiol., 26, 1097 (1997)), while KipA binds to KipI, which is an auto-phosphorylation inhibitor of KinA, to avoid the sporulation suppressive action thereof (Genes Dev., 11, 2569 (1997)). Also, PhrA inhibits the function of RapA which is a dephosphorylation enzyme for phosphorylated Spo0F (Proc. Natl. Acad. Sci. USA, 94, 8612 (1997)). KinA, KinB, KinC, Spo0F, Spo0B, Spo0A, KapB, KipI, KipA, RapA and PhrA are encoded by the genes kinA, kinB, kinC, spo0F, spo0B, spo0A, kapB, kipI, kipA, rapA and phrA, respectively.

Accompanied by an increase in the concentration of Phosphorylated Spo0A, induction of repressor AbrB which suppresses the expression of a structural gene of SigH (sigH) is suppressed, and as a result, transcription of sigH is induced in a SigA-dependent manner (J. Bacteriol., 173, 521 (1991)). Additionally, while the Phosphorylated Spo0A transcription regulatory function is inhibited by Soj which is involved in the chromosome separation, Spo0J which is also involved in the chromosome separation suppresses such action of Soj (J. Bacteriol., 182, 3446, 2000). Soj and Spo0J are encoded by soj gene and spo0J gene, respectively. After the activation of SigH, the cytoplasm of *Bacillus subtilis* is partitioned by the formation of an asymmetric septum, into the mother cell side and the daughter cell side. Subsequently, on the daughter cell side, Phosphorylated Spo0A and SigH are conjugated to induce the transcription of an operon (spoIIAA-spoIIAB-sigF) containing the structural gene of SigF (sigF) (Gene, 101, 113 (1991)), and on the mother cell side, Phosphorylated Spo0A and SigA are conjugated to induce the transcription of an operon (spoIIGA-sigE) containing the structural gene of SigE precursor (sigE) (J. Bacteriol., 169, 3329 (1987)). There exists two-stage suppression in which SigF is functionally suppressed by an anti-sigma factor, SpoIIAB, and an anti-anti-sigma factor, SpoIIAA, suppresses the action of SpoIIAB. That is, while the functional deletion of SpoIIAA leads to the inhibition of sporulation as in the case of the functional deletion of SigF, the functional deletion of SpoIIAB is also known to inhibit sporulation (Proc. Natl. Acad. Sci. USA, 87, 9221 (1990); J. Bacteriol., 173, 6678 (1991)). Furthermore, the activation is controlled by SpoIIE which is a dephosphorylation enzyme for SpoIIAA (Genes Cells, 1, 881 (1996)), and activated SigF induces the transcription of the structural gene of SpoIIR, which is a signal transduction protein. It is conceived that SpoIIR secreted from the daughter cell side activates SpoIIGA which is a SigE precursor activating protease localized in the asymmetric septum on the mother cell side, and thereby activation of SigE takes place (Proc. Natl. Acad. Sci. USA, 92, 2012 (1995)). SpoIIAA, SpoIIAB, SpoIIE, SpoIIR and SpoIIGA are encoded by spoIIAA, spoIIAB, spoIIE, spoIIR and spoIIGA genes, respectively. Further, on the daughter cell side, SigF induces the transcription of the structural gene of SigG (sigG), and on the mother cell side, SigE induces the transcription of the structural genes of SigK (spoIIIC gene and spoIVCB gene). However, the activation of SigG on the daughter cell side occurs after the activation of SigE on the mother cell side, and the activation of SigK occurs thereafter on the mother cell side (Mol. Microbiol., 31, 1285 (1999)).

Among the genes described above, the genes which inhibit the process of sporulation when deleted or inactivated are, as obvious from FIG. 2, kinA, kinB, kinC, spo0F, spo0B, spo0A, kapB, kipA, phrA, spo0J, sigH, sigF, sigE, spoIIAA, spoIIAB, spoIIE, spoIIR, spoIIGA, sigG, spoIIIC and spoIVCB genes. The sporulation-associated genes to be deleted or inactivated in the present invention are preferably selected from these genes belonging to *Bacillus subtilis*, and more preferably selected from sigF gene, sigE gene and phrA gene of *Bacillus subtilis*.

The sigF gene is a gene for encoding a sigma factor which is responsible for the expression of genes occurring in the daughter cell side from stage II on, where the asymmetric septum is formed in the *Bacillus subtilis* cells, during the sporulation stages, while the sigE gene is a gene for encoding a sigma factor which is responsible for the expression of genes occurring in the mother cell side from stage II on, where the asymmetric septum is formed in the *Bacillus subtilis* cells, during the sporulation stages.

Furthermore, the phrA gene is one of the genes involved in the mechanism of intercellular information transmission needed in the case of sensing changes in the external growth environment and responding thereto in various ways, and the gene product is secreted outside the cell for the moment. It is reported that the gene is, after being processed outside the cell, ingested into the cell as a pentapeptide, and is bound to RapA protein which controls phosphorylation of Spo0F in the phosphor-relay system for transmitting signals for the initiation of sporulation, thereby participating in the signal transduction for the initiation of sporulation (Proc. Natl. Acad. Sci. USA, 94, 8612 (1997)).

The gene number and function of each of the above-mentioned genes are summarized in Table 6.

A gene corresponding to the sporulation-associated genes such as kinA, kinB, kinC, spo0F, spo0B, spo0A, kapB, kipA, phrA, spo0J, sigH, sigF, sigE, spoIIAA, spoIIAB, spoIIE, spoIIR, spoIIGA, sigG, spoIIIC and spoIVCB, refers to a gene having the substantially same function as that of any one of the above genes, and for example, there may be mentioned a gene derived from another microorganism, preferably one derived from a bacterium of the genus *Bacillus*, having a base sequence at least 70%, preferably at least 80%, more preferably at least 90%, even more preferably at least 95%, and still more preferably at least 98%, identical to the base sequence of any one of those genes. Additionally, the identity of base sequences here is calculated according to the Lipman-Pearson method (Science, 227, 1435 (1985)).

Deletion or inactivation of such genes may be deletion or inactivation of an individual among the aforementioned various genes, or may be deletion or inactivation of a combination of two or more thereof. Further, enhancement, or deletion or inactivation of a gene other than the subject gene may also be performed in parallel. Additionally, the deletion or inactivation of a gene includes substitution or deletion of a part or all of bases in the gene, as well as insertion of bases into the gene.

As for the order of the deletion or inactivation of a group of genes or a gene, there may be mentioned a method of intentionally deleting or inactivating the subject gene (target gene), as well as a method of mutating a random gene through deletion or inactivation, and then performing evaluation of protein productivity and genetic analysis by appropriate methods.

Figure 3:
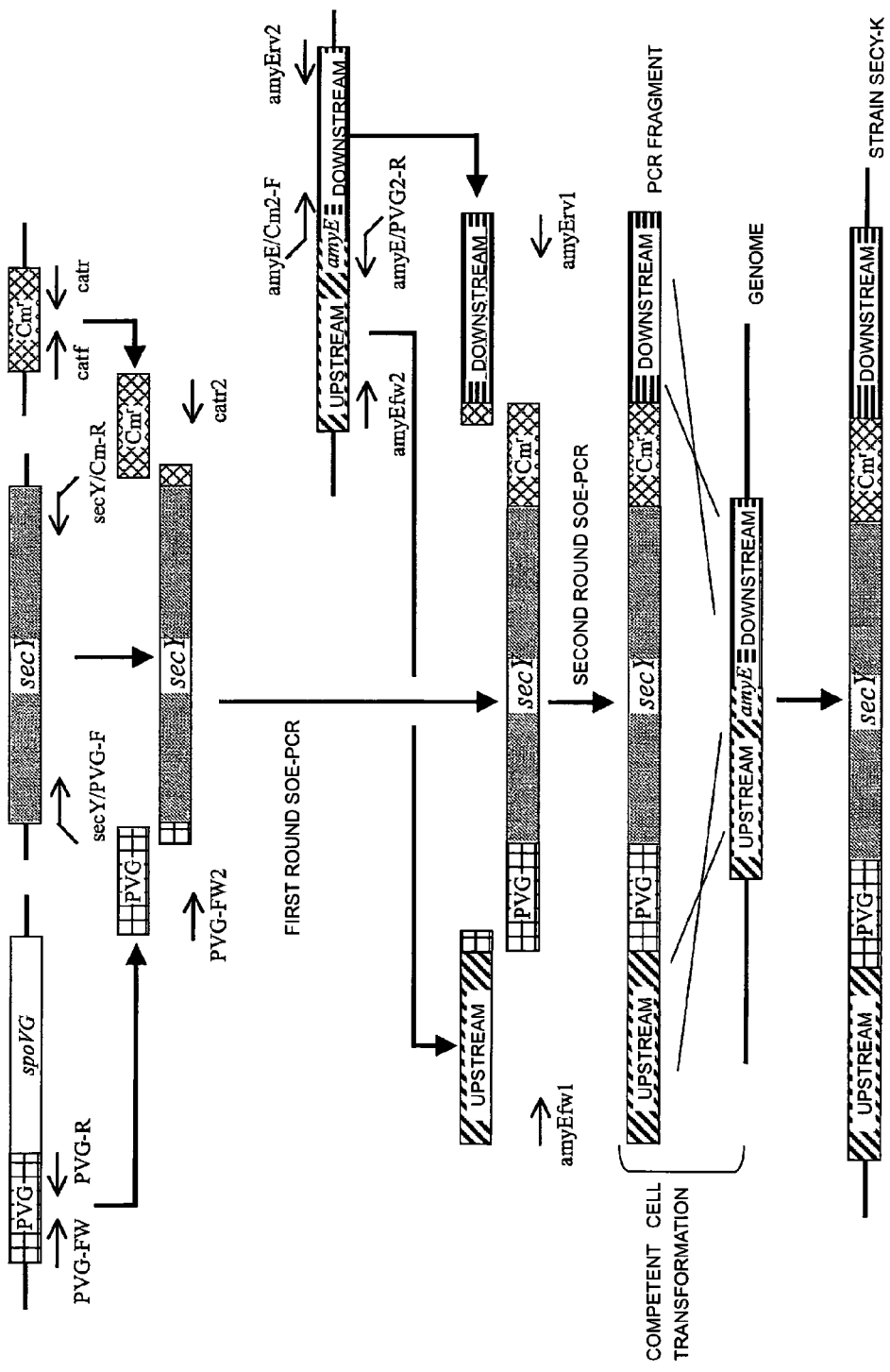
FIG. 3 is a schematic diagram showing a method for preparing a DNA fragment for the production of a strain with enhanced secY expression, through SOE-PCR.

To delete or inactivate a target gene, for example, a method involving homologous recombination may be used. That is, a cyclic recombinant plasmid obtained by cloning a DNA fragment containing a part of the target gene in an appropriate plasmid can be transfected into the cells of a parent microorganism, so that the target gene on the genome of the parent microorganism is split by homologous recombination in some region of the target gene, thereby inactivating the target gene. Alternatively, it is also possible to substitute a target gene on the genome with a deleted or inactivated gene fragment, by constructing a target gene inactivated through mutation such as base substitution or base insertion, or a linear DNA fragment containing the upstream and downstream regions of the target gene but not containing the target gene, as shown in FIG. 3, according to a PCR method or the like, and transfecting the resultant into the cells of a parent microorganism, to thereby cause double crossover homologous recombination at two sites exterior to the mutation site within the target gene on the genome of the parent microorganism, or on the upstream side and downstream side of the target gene.

Particularly, in the case of using *Bacillus subtilis* as the parent microorganism for constructing the microorganism of the present invention, several reports are already available on the method of deleting or inactivating a target gene by homologous recombination (Mol. Gen. Genet., 223, 268 (1990) and the like), and thus the host microorganism of the present invention can be obtained by repeating such methods.

The deletion or inactivation of random genes can also be performed by a method of inducing homologous recombination, such as the above-described method using a randomly cloned DNA fragment, or by irradiating a parent microorganism with radiation.

Hereinafter, the method of deletion by double crossover using a DNA fragment for deletion which is prepared according to the SOE (splicing by overlap extension)-PCR method (Gene, 77, 61 (1989)) will be more specifically explained, but the method of gene deletion in the present invention is not intended to be limited to the following.

Figure 4:
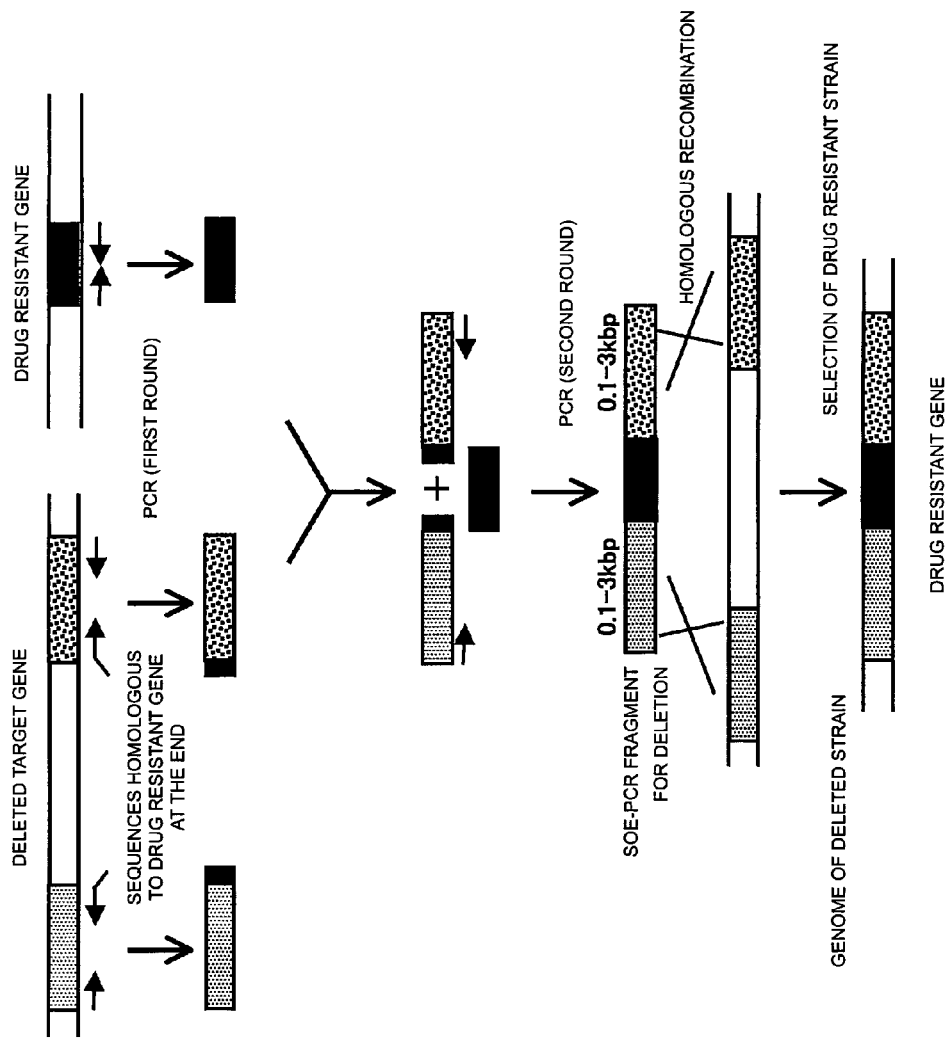
FIG. 4 is a schematic diagram showing the deletion of a target gene through a double crossover method using SOE-PCR fragment.

The DNA fragment for deletion used in the present method is a fragment prepared by inserting a drug resistance marker gene fragment between a fragment of about 0.1 to 3 kb in size, preferably 0.4 to 3 kb, which is adjacent to the upstream of the gene to be deleted, and a fragment of about 0.1 to 3 kb in size, preferably 0.4 to 3 kb, which is adjacent to the downstream of the gene to be deleted. First, three fragments of an upstream fragment and a downstream fragment of the gene to be deleted, and a drug resistance marker gene fragment are prepared by the first round of PCR, and at this time, a primer designed such that, for example, a sequence of 10 to 30 base pairs on the upstream side of the drug resistance marker gene is added to the downstream end of the upstream fragment, and conversely, a sequence of 10 to 30 base pairs on the downstream side of the drug resistance marker gene is added to the upstream end of the downstream fragment, is used (FIG. 4).

Subsequently, the three kinds of PCR fragments prepared in the first round are used as templates, and the second round of PCR is performed using the upstream side primer of the upstream fragment and the downstream primer of the downstream fragment. Thereby, annealing occurs with the drug resistance marker gene fragment in the drug resistance marker gene sequences added to the downstream end of the upstream fragment and the upstream end of the downstream fragment, and as a result of PCR amplification, a DNA fragment having a drug resistance marker gene inserted between an upstream side fragment and a downstream side fragment, can be obtained (FIG. 4).

In the case of using a chloramphenicol resistance gene as the drug resistance marker gene, DNA fragments for deletion of various genes are obtained by performing SOE-PCR under conventional conditions that are shown in literatures (PCR Protocols. Current Methods and Applications, Edited by B. A. White, Humana Press, p. 251, 1993; Gene, 77, 61 (1989)), using the primer set indicated in Table 1 and using an enzyme kit for general PCR, such as Pyrobest DNA polymerase (Takara Shuzo Co., Ltd.).

When the DNA fragment for deletion thus obtained is transfected into cells by a competent method or the like, gene recombination occurs within the cells, in the homologous regions upstream and downstream to the gene to be deleted, where identity exists, and cells in which the desired gene has been substituted with the drug resistance gene, can be isolated through selection based on the drug resistance marker. That is, when a DNA fragment for deletion prepared using the primer set indicated in Table 1 is transfected, colonies growing on an agar medium containing chloramphenicol may be isolated and confirmed on that the desired gene on the genome is substituted with the chloramphenicol resistance gene by a PCR method using the genome as the template, or the like.

The microorganism of the present invention can be obtained by transfecting a gene, which encodes a desired protein or a desired polypeptide, into the microorganism thus produced. Here, the term "desired protein or polypeptide" means a protein or polypeptide for which one of the purposes is production or purification. Also, with regard to the "microorganism having a gene which encodes a desired protein or polypeptide," the gene is meant to include the genes originally possessed by the microorganism, as well as genes not originally possessed by the microorganism, that is, foreign genes.

The desired protein or desired polypeptide is not particularly limited, and examples thereof include various industrial enzymes or physiologically active peptides used in detergents, foods, fabrics, feedstuff, chemicals, medicine, diagnosis and the like, while industrial enzymes are preferred. Also, in terms of function of the industrial enzymes, oxidoreductases, transferases, hydrolases, lyases, isomerases, ligases/synthetases, and the like are included, and there may be favorably mentioned hydrolases such as cellulases, γ-amylases and proteases.

As for the proteases, proteases derived from microorganisms, preferably those derived from bacteria of the genus *Bacillus*, more preferably those derived from *Bacillus clausii* strain KSM-K16 (FERM BP-3376), may be mentioned. More specific examples of alkali proteases derived from *Bacillus clausii* strain KSM-K16 include an alkali protease derived from a bacterium of the genus *Bacillus*, comprising an amino acid sequence from amino acid No. 1 to amino acid No. 380 of the amino acid sequence set forth in SEQ ID NO: 4, or a protease comprising an amino acid sequence having 70%, preferably 80%, more preferably at least 90%, even more preferably 95%, and still more preferably at least 98%, identity to the above amino acid sequence.

As for the cellulase, there may be mentioned cellulases belonging to Family 5 among the class of polysaccharide hydrolases (Biochem. J., 280, 309 (1991)), and among them, cellulases derived from microorganisms, particularly those derived from bacteria of the genus *Bacillus*, may be mentioned. For example, cellulases derived from *Bacillus* sp. strain KSM-S237 (FERM BP-7875) and *Bacillus* sp. strain KSM-64 (FERM BP-2886) may be mentioned, and suitable examples thereof include an alkali cellulase derived from a bacterium of the genus *Bacillus*, comprising an amino acid sequence from amino acid No. 1 to amino acid No. 795 of the amino acid sequence set forth in SEQ ID NO: 6, or an alkali cellulase derived from a bacterium of the genus *Bacillus*, comprising an amino acid sequence from amino acid No. 1 to amino acid No. 793 of the amino acid sequence set forth in SEQ ID NO: 8, or a cellulase comprising an amino acid sequence having 70%, preferably 80%, more preferably at least 90%, even more preferably at least 95%, and still more preferably at least 98%, identity to the above amino acid sequence.

Furthermore, as for the γ-amylase, there may be mentioned γ-amylases derived from microorganisms, preferably those derived from bacteria of the genus *Bacillus*, and more preferably those derived from *Bacillus* sp. strain KSM-K38.

It is desirable that the gene of the desired protein or desired polypeptide to be transfected into the microorganism of the present invention is coupled with one or more regions selected from the control regions associated with transcription, translation and secretion of the gene, namely, a transcription initiation control region containing a promoter and a transcription initiation point, a translation initiation control region containing a ribosome binding site and an initiation codon, and a secretion signal peptide region, in the upstream in an adequate form. In particular, a gene having three bound regions, including a transcription initiation control region, a translation initiation control region and a secretion signal peptide region, is preferred, and also, it is desirable that the secretion signal peptide region is one derived from a cellulase gene of a bacterium of the genus *Bacillus*, while the transcription initiation control region and translation initiation control region are regions of 0.6 to 1 kb in size upstream to the cellulase gene, and these regions are adequately coupled with the gene of the desired protein or desired polypeptide. For example, it is desirable that the cellulase gene derived from a bacterium of the genus *Bacillus*, that is, strain KSM-5237 (FERM BP-7875) or strain KSM-64 (FERM BP-2886), and the transcription initiation control region, translation initiation control region and secretion signal peptide region of the cellulase gene are adequately coupled with the structural gene of a desired protein or desired polypeptide. More specifically, it is desirable that a DNA fragment comprising a base sequence from base No. 1 to base No. 659 of the base sequence set forth in SEQ ID NO: 5, or a base sequence from base No. 1 to base No. 696 of the base sequence set forth in SEQ ID NO: 7, or a base sequence having at least 70%, preferably at least 80%, more preferably at least 90%, even more preferably at least 95%, and still more preferably at least 98%, identity to the above base sequence, or a DNA fragment comprising a base sequence resulting from deletion, substitution or addition of a part of any of the above base sequences, is adequately coupled with the structural gene of a desired protein or desired polypeptide. Additionally, the DNA fragment comprising a base sequence resulting from deletion, substitution or addition of a part of the above base sequence as used herein means a DNA fragment which has a part of the above base sequence deleted, substituted or added, but maintains the function associated with the transcription, translation and secretion of a gene.

The introduction of such gene encoding a desired protein or desired polypeptide can be performed, for example, through (1) introduction by a vector, or (2) insertion into the genome. In the case of the (1) introduction by a vector, a vector containing a gene which encodes a desired protein or desired polypeptide, and is coupled in the upstream with one or more regions selected from the control regions associated with transcription, translation and secretion of the gene, namely, a transcription initiation control region containing a promoter and a transcription initiation point, a translation initiation control region containing a ribosome binding site and an initiation codon, and a secretion signal peptide region, in an adequate form, may be introduced by an appropriate transformation method such as a competent cell transformation method, a protoplast transformation method or an electroporation method. Here, the vector is not particularly limited as long as it is an appropriate carrier nucleic acid molecule for transfecting a desired gene into a host so as to propagate and express the gene, and there may be mentioned plasmids, and also, for example, artificial chromosomes such as YAC and BAC, vectors using transposon, cosmids and the like. Examples of the plasmid include pUB110 and pHY300PLK.

Furthermore, the (2) insertion into the genome may be performed, for example, using a method involving homologous recombination. That is, a DNA fragment having a part of a chromosome region for inducing introduction bound to a gene encoding a desired protein or desired polypeptide, can be incorporated into the genome by transfecting the DNA fragment into the cells of a microorganism, and inducing homologous recombination in some part of the chromosome region. Here, the chromosome region for inducing introduction is not particularly limited, but a non-essential gene region or a non-gene region upstream to a non-essential gene region is preferred.

The production of a desired protein or polypeptide using the recombinant microorganism of the present invention may be performed by inoculating the bacterial strain into a medium containing assimilable carbon sources, nitrogen sources and other essential components, culturing the strain by a conventional microorganism culturing method, and after completion of the culture, collecting and purifying the protein or polypeptide. As described in the Examples that are described later, an improvement in the productivity for a desired protein or polypeptide is achieved as compared with the case of using a microorganism that has not been altered in the gene.

Hereinafter, a method for constructing the recombination microorganism of the present invention, and a method for producing a cellulase and an amylase using the recombinant microorganism will be described in detail.

EXAMPLES

In the polymerase chain reaction (PCR) for the amplification of DNA fragments in the following Examples, DNA amplification was performed using a GeneAmp PCR System (Applied Biosystems, Inc.) and using Pyrobest DNA Polymerase (Takara Bio, Inc.) and accessory reagents. The composition of the PCR reaction solution was prepared by adding 1 µL of appropriately diluted template DNA, 20 pmol each of a sense primer and an antisense primer, and 2.5 U of Pyrobest DNA Polymerase, and adjusting the total amount of the reaction solution to 50 µL. PCR was performed under the reaction conditions of repeating 30 rounds of three-stage temperature change of 10 seconds at 98° C., 30 seconds at 55° C., and 1 to 5 minutes at 72° C. (adjusted in accordance with the desired amplification product. A rough standard is 1 minute per 1 kb), and then allowing the reaction to proceed for 5 minutes at 72° C.

Furthermore, in the following Examples, the upstream and downstream of a gene refer not to the locations from the replication initiation point, but the upstream indicates a region following the 5'-end of a gene or region of interest in various operations and processes, while the downstream indicates a region following the 3'-end of a gene or region of interest in various operations and processes.

Furthermore, the names of the respective genes and gene regions in the following Examples are described on the basis of the genome data of *Bacillus subtilis* reported in Nature, 390, 249-256 (1997) and published in the Internet at the website of JAFAN: Japan Functional Analysis Network for *Bacillus subtilis* (BSORF DB) (bacillus.genome.ad.jp/, renewed on Mar. 10, 2004).

Transformation of *Bacillus subtilis* was performed in the following manner. Specifically, a strain of *Bacillus subtilis* was cultured with shaking in SPI medium (0.20% ammonium sulfate, 1.40% dipotassium hydrogen phosphate, 0.60% potassium dihydrogen phosphate, 0.10% trisodium citrate dihydrate, 0.50% glucose, 0.02% casamino acid (Difco Laboratories, Inc.), 5 mM magnesium sulfate, 0.25 µM manganese chloride, and 50 µg/mL tryptophan) at 37° C., until the value of degree of growth (OD600) reaches about 1. After the culturing with shaking, some of the culture solution was inoculated into a 9-fold amount of SPII medium (0.20% ammonium sulfate, 1.40% dipotassium hydrogen phosphate, 0.60% potassium dihydrogen phosphate, 0.10% trisodium citrate dihydrate, 0.50% glucose, 0.01% casamino acid (Difco Laboratories, Inc.), 5 mM magnesium sulfate, 0.40 µM manganese chloride, and 5 µg/mL tryptophan), and the cells were further cultured with shaking until the value of degree of growth ($OD_{600}$) reached about 0.4. Thus, competent cells of *Bacillus subtilis* were prepared.

Subsequently, to 100 µL of the competent cell suspension thus prepared (culture solution in SPII medium), 5 µL of a solution containing various DNA fragments (SOE-PCR reaction solution or the like) was added, the mixture was incubated with shaking for 1 hour at 37° C., and the total amount was smeared onto LB agar medium (1% tryptophan, 0.5% yeast extract, 1% NaCl, and 1.5% agar) containing an appropriate drug. After stationary culture at 37° C., grown colonies were isolated as a transformant. The genome of the obtained transformant was extracted, and it was confirmed by PCR using the genome as the template, that a desired alteration in the genome structure was achieved.

The transfection of a gene encoding a desired protein or polypeptide into a host microorganism was performed following any of the competent cell transformation method (J. Bacteriol., 93, 1925 (1967)), the electroporation method (FEMS Microbiol. Lett., 55, 135 (1990)), and the protoplast transformation method (Mol. Gen. Genet., 168, 111 (1979)).

As for the culture for protein production by the recombinant microorganism, LB medium (1% tryptophan, 0.5% yeast extract, and 1% NaCl), 2×YT medium (1.6% tryptophan, 1% yeast extract, and 0.5% NaCl), 2×L-maltose medium (2% tryptophan, 1% yeast extract, 1% NaCl, 7.5% maltose, and 7.5 ppm manganese sulfate tetra- or pentahydrate), or CSL fermentation medium (2% yeast extract, 0.5% corn steep liquor (CSL), 0.05% magnesium chloride heptahydrate, 0.6% urea, 0.2% L-tryptophan, 10% glucose, 0.15% sodium dihydrogen phosphate, and 0.35% disodium hydrogen phosphate, pH 7.2) were used.

Example 1

Construction of Strain Overexpressing secY Gene

Construction of a variant overexpressing secY gene was performed as follows (see FIG. 3). A 0.2 kb fragment (A) containing the transcription initiation control region and the ribosome binding site of spoVG gene, and a 1.3 kb fragment (B) containing spoVG gene were amplified by PCR using the genome DNA extracted from *Bacillus subtilis* strain 168 as the template, and using primer sets of PVG-FW and PVG-R, and secY/PVG-F and secY/Cm-R. Furthermore, a 0.9 kb fragment (C) containing chloramphenicol (Cm) resistance gene was amplified by PCR using plasmid pC194 (J. Bacteriol., 150(2), 815 (1982)) as the template, and using the primer set of catf and catr shown in Table 1.

Next, a DNA fragment (D) of 2.2 kb in size, in which the three fragments of (A), (B) and (C) were coupled in this order, the transcription initiation control region and the ribosome binding site of spoVG gene were linked to the upstream of secY gene (linked such that the initiation codon of secY gene is located at the location of the initiation codon of spoVG gene), and a Cm resistance gene was bound downstream thereto, was obtained by using a mixture of the obtained three fragments of (A), (B) and (C) as a template, and performing SOE-PCR using the primer set of PVG-FW2 and catr2 shown in Table 1. Subsequently, a 1.0 kb fragment (E) containing the region on the 5'-end of amyE gene, and a 1.0 kb fragment (F) containing the region on the 3'-end of amyE gene were amplified by PCR, using the genome data extracted from *Bacillus subtilis* strain 168 as the template, and using the primer sets of amyEfw2 and amyE/PVG2-R and amyE/Cm2-F and amyErv2 shown in Table 1.

Subsequently, a DNA fragment (G) having a total base length of 4.2 kb, in which the three fragments of (E), (D) and (F) were bound in this order, secY gene was linked to the downstream of the transcription initiation control region and the ribosome binding site of spoVG gene, and a DNA fragment of 2.2 kb in size coupled with a chloramphenicol resistance gene in the downstream thereto was inserted in the center of amyE gene, was obtained by using a mixture of the obtained three fragments of (E), (F) and (D) as a template, and performing SOE-PCR using the primer set of amyEfw1 and amyErv1 shown in Table 1.

Using the obtained DNA fragment (G) of 4.2 kb, *Bacillus subtilis* strain 168 was transformed by the competent cell method, and colonies growing on LB agar medium containing (10 µg/mL) were isolated as a transformant. Amplification of DNA fragments of 2.5 kb and 3.1 kb in size, respectively, was confirmed by performing PCR using the genome DNA extracted from the obtained transformant as a template, and using the primer sets of amyEfw2 and secY/Cm-R, and secY/PVG-F and amyErv2 shown in Table 1, and it was confirmed that a DNA fragment in which secY gene was linked downstream to the transcription initiation control region and the ribosome binding site of spoVG gene, was inserted at the amyE gene site on the genome of *Bacillus subtilis* strain 168. The strain thus obtained was designated as strain secY-K.

TABLE 1

| Name of Primer | Sequence (5'-3') | SEQ ID NO. |
|---|---|---|
| PVG-FW | GTTAGTCGAGATCGAAGTTA | 10 |
| PVG-R | AGTAGTTCACCACCTTTTCC | 11 |
| secY/PVG-F | GGAAAAGGTGGTGAACTACTATGTTGTTT AAAACAATCTCCAA | 12 |
| secY/Cm-R | ATGGGTGCTTTAGTTGAAGACTAGTTTTT CATAAATCCAC | 13 |
| catf | CAACTAAAGCACCCATTAG | 14 |
| catr | CTTCAACTAACGGGGCAG | 15 |

TABLE 1-continued

| Name of Primer | Sequence (5'-3') | SEQ ID NO. |
| --- | --- | --- |
| PVG-FW2 | TAAGAAAAGTGATTCTGGGA | 16 |
| catr2 | CTCATATTATAAAAGCCAGTC | 17 |
| amyEfw2 | GGAGTGTCAAGAATGTTTGC | 18 |
| amyE/PVG2-R | TCCCAGAATCACTTTTCTTAATCATCGCTCATCCATGTCG | 19 |
| amyE/Cm2-F | GACTGGCTTTTATAATATGAGGTTTAGGCTGGGCGGTGATA | 20 |
| amyErv2 | TCAATGGGGAAGAGAACC | 21 |
| amyErv1 | TCAAAACCTCTTTACTGCCG | 22 |
| amyErv1 | CACGTAATCAAAGCCAGGCT | 23 |
| spf | ATCGATTTTCGTTCGTG | 24 |
| spr | CATATGCAAGGGTTTATTG | 25 |
| sigF-FW | GAAGAAAGCCGGGTTTATCA | 26 |
| sigF/Sp-R | CACGAACGAAAATCGATCTGAGCGTTTTTGCCGTTTT | 27 |
| sigF/Sp-F | CAATAAACCCTTGCATATGTCTGCAGTGCAGGCTAGCTT | 28 |
| sigF-RV | CCCGACGAACAAACCTGCCA | 29 |
| sigF-FW2 | CGAATGACCACTAGTTTTGT | 30 |
| sigF-RV2 | TGAAGCGTCTCCCATCCCCC | 31 |
| sigE-FW | AGTCAGATGTGAAAATCTATT | 32 |
| sigE/Sp-R | CACGAACGAAAATCGATCTTCCTCTCCCTTCTAAATG | 33 |
| sigE/Sp-F | CAATAAACCCTTGCATATGAAAATTTTATGGTTAGAACCC | 34 |
| sigE-RV | CCTTACTTTTTCCAAAACGT | 35 |
| sigE-FW2 | CTCACGGCATTTATTTTAAAA | 36 |
| sigE-RV2 | GCTTTTCATTATTGATGAATAT | 37 |
| phrA-FW | AGAAGACCAAGATTTGCTGC | 38 |
| phrA/Sp-R | CACGAACGAAAATCGATATGAAATGTTTTCCCTTCTG | 39 |
| phrA/Sp-F | CAATAAACCCTTGCATATGGGTTCATGCAGGTGAAAC | 40 |
| phrA-RV | ACTGGCCCCGTGTGATGCGG | 41 |
| phrA-FW2 | GAGTTTTCAGAATTGTTAGAA | 42 |
| phrA-RV2 | GAAGAGACTGCAGCTTTTT | 43 |
| S237pKAPpp-F | ACTTTAAAAATATTTAGGAGGTAATATGAAGAAACCGTTGGGGAAA | 44 |
| KAPter-R(BglII) | GGGAGATCTTCAGCGATCTATTTCTCTTTTTC | 45 |
| S237ppp-F2(BamHI) | CCCGGATCCAACAGGCTTATATTTA | 46 |
| S237pKAPpp-R | TTTCCCCAACGGTTTCTTCATATTACCTCCTAAATATTTTTAAAGT | 47 |
| 237UB1 | TTGCGGATCCAACAGGCTTATATTTAGAGGAAATTTC | 48 |
| 237DB1 | TTGCGGATCCAACAACTCTGTGTCCAGTTATGCAAG | 49 |
| rsiX-FW | ATTCCAGTTACTCGTAATATAGTTG | 50 |
| rsiX/Cm-R | CTAATGGGTGCTTTAGTTGACTTCATCATCCATTAGCTC | 51 |
| rsiX/Cm-F | CTGCCCCGTTAGTTGAAGCTGCTCCAAATCCGATTTCC | 52 |
| rsiX-RV | GTCCTGCATTTTTCGAAGTCTGG | 53 |
| rsiX-FW2 | ACTCCGGGTCTGGCATACCG | 54 |
| rsiX-RV2 | ACATCTGGAAGATAAAATTGT | 55 |
| yacP-FW | CAGGCTGAGATCCTATTTTT | 56 |
| yacP/Cm-R | CTAATGGGTGCTTTAGTTGGGGTCTTTATTCTCCCACAG | 57 |
| yacP/Cm-F | CTGCCCCGTTAGTTGAAGGTTGACGCTTTTTTGCCCAA | 58 |
| yacP-RV | ACGCATGTAAAAGACCTCCA | 59 |
| yacP-FW2 | GAGGCAGAAATGCCAAGTCA | 60 |
| yacP-RV2 | TTGCAAGTACTGCAGTATTT | 61 |
| yvdE-FW | CTTCCTCCATTAAAAAGCCG | 62 |
| yvdE/Cm-R | CTAATGGGTGCTTTAGTTGTTTCATCCCCTCCTTATCTG | 63 |
| yvdE/Cm-F | CTGCCCCGTTAGTTGAAGGCGCCTTATTCTGTTATCGG | 64 |
| yvdE-RV | CGGCATATCAGCTGTAAAAG | 65 |
| yvdE-FW2 | TTTCATCCATTTTTCTGCATC | 66 |
| yvdE-RV2 | CAGTCCTTATAGCGGGATTG | 67 |
| yurK-FW | CTTCAGCCGCTTTGCTTTTT | 68 |
| vurK/Cm-R | CTAATGGGTGCTTTAGTTGAGGGTAGCCTCCTTTTAACC | 69 |
| vurK/Cm-F | CTGCCCCGTTAGTTGAAGCAGGCATAAAAAACGAGACA | 70 |
| yurK-RV | GTCCTGCTGGCGGGGTTAAC | 71 |
| yurK-FW2 | TGCTGCTGTTCTATGATGCC | 72 |
| yurK-RV2 | TTGTCCGCGGGATTGCAAGC | 73 |
| yhdQ-FW | TCACAAATCCAAGCGTTCGA | 74 |
| yhdQ/Cm-R | CTAATGGGTGCTTTAGTTGCACGTTATAGTTATGAGAATA | 75 |
| yhdQ/Cm-F | CTGCCCCGTTAGTTGAAGAACCATTTTATCTAACAGGAG | 76 |
| yhdQ-RV | TGTGGACCCTCTCTTTTTGC | 77 |
| yhdQ-FW2 | GTCCAATCCGATATACCCGA | 78 |
| yhdQ-RV2 | AGGGTTGACGAATTGAGAAA | 79 |
| glcT-FW | AAGCCGGTGTCTCTGTTACA | 80 |

TABLE 1-continued

| Name of Primer | Sequence (5'-3') | SEQ ID NO. |
|---|---|---|
| glcT/Cm-R | CTAATGGGTGCTTTAGTTGTCAATACCTCATATCGTACA | 81 |
| glcT/Cm-F | CTGCCCCGTTAGTTGAAGAATTTCATAAATTCAGTTTATCC | 82 |
| glcT-RV | CTTATAGCTGAAGAATTCATA | 83 |
| glcT-FW2 | AAAAAGAGTGTTTGAGGCAA | 84 |
| glcT-RV2 | GTTCAATCACCCCGAAGATA | 85 |

Example 2

Substitution of sigF Gene in the Genome with Drug Resistance Gene

A method for substituting sigE gene in the genome with a drug resistance gene will be described on the basis of FIG. 4.

The genome DNA extracted from *Bacillus subtilis* strain 168 was used as a template, a 1.0 kb fragment (A) adjacent to the upstream of sigE gene in the genome was amplified by PCR using the primer set of sigF-FW and sigF/Sp-R shown in Table 1. Also, the above-mentioned genome DNA was used as a template, and a 1.0 kb fragment (B) adjacent to the downstream of sigF gene in the genome was amplified by PCR using the primer set of sigF/sp-F and sigF-RV.

Furthermore, a spectinomycin (Sp) resistance gene region (C) of 1.2 kb in size was prepared by PCR using plasmid pDG1727 (Gene, 167, 335 (1995)) DNA as a template, and using the primer set of spf and spr shown in Table 1.

Subsequently, as shown in FIG. 4, a mixture of the obtained three fragments of 1.0 kb fragment (A), 1.0 kb fragment (B) and Sp resistance gene region (C) was used as a template, and a DNA fragment (D) of 2.8 kb in which the three fragments were contained in the order of the 1.0 kb fragment (A), the Sp resistance gene region (C) and the 1.0 kb fragment (B), was obtained according to the SOE-PCR method using the primer set of sigF-FW2 and sigF-RV2 shown in Table 1.

Then, transformation of the strain 168 was performed using the obtained DNA fragment (D), according to the competent cell transformation method. After the transformation, colonies growing on an LB agar medium containing spectinomycin (100 μg/mL) were isolated as a transformant. The genome DNA of the obtained transformant was extracted, and it was confirmed that sigF gene was substituted with the Sp resistance gene by PCR. As such, a sigF gene deleted strain (strain ΔsigF) was constructed. Furthermore, a strain in which sigF gene was substituted with the Sp resistance gene in the genome of strain secY-K (strain secYKΔsigb) was constructed using the strain secY-K that was constructed in Example 1 by changing the strain to *Bacillus subtilis* strain 168 in the transformation.

Example 3

Substitution of sigE Gene and phrA Gene in the Genome with Drug Resistance Gene

Substitution of sigE gene and phrA gene in the genome of strain 168 with a spectinomycin resistance gene was performed in the same manner as in the substitution of sigE gene with a drug resistance gene as shown in Example 2, to thus construct a sigE gene deleted strain (strain ΔsigE) and a phrA gene deleted strain (strain ΔphrA). For the construction of the respective strains, the primers shown in Table 1 were used, and the correspondence of the respective primers to the primers used in the construction of strain ΔsigF is shown in Table 2.

TABLE 2

| | For deletion of sigF gene | For deletion of sigE gene | For deletion of phrA gene | For deletion of rsiX gene | For deletion of yacP gene | For deletion of yvdE gene | For deletion of yurK gene | For deletion of yhdQ gene | For deletion of glcT gene |
|---|---|---|---|---|---|---|---|---|---|
| Amplification of fragment (A) | sigF-FW | sigE-FW | phrA-FW | rsiX-FW | yacP-FW | yvdE-FW | yurK-FW | yhdQ-FW | glcT-FW |
| | sigF/Cm-R | sigE/Cm-R | phrA/Cm-R | rsiX/Cm-R | yacP/Cm-R | yvdE/Cm-R | yurK/Cm-R | yhdQ/Cm-R | glcT/Cm-R |
| Amplification of fragment (B) | sigF/Cm-F | sigE/Cm-F | phrA/Cm-F | rsiX/Cm-F | yacP/Cm-F | yvdE/Cm-F | yurK/Cm-F | yhdQ/Cm-F | glcT/Cm-F |
| | sigF-RV | sigE-RV | phrA-RV | rsiX-RV | yacP-RV | yvdE-RV | yurK-RV | yhdQ-RV | glcT-RV |
| Amplification of fragment (C) | spf | spf | spf | catf | catf | catf | catf | catf | catf |
| | spr | spr | spr | catr | catr | catr | catr | catr | catr |
| Amplification of fragment (D) | sigF-FW2 | sigE-FW2 | phrA-FW2 | rsiX-FW2 | yacP-FW2 | yvdE-FW2 | yurK-FW2 | yhdQ-FW2 | glcT-FW2 |
| | sigF-RV2 | sigE-RV2 | phrA-RV2 | rsiX-RV2 | yacP-RV2 | yvdE-RV2 | yurK-RV2 | yhdQ-RV2 | glcT-RV2 |

By substituting sigE gene or phrA gene on the genome of strain secY-K constructed in Example 1, with a spectinomycin resistance gene, strain secYKΔsigE and strain secYKΔphrA were constructed.

Example 4

Evaluation of Secretion and Production of Alkali Protease

Evaluation of the productivity for heterologous proteins of the strain secY-K, strain secYKΔsigF, strain secYKΔsigE and strain secYKΔphrA obtained in Examples 1 to 3 was performed as follows, using the productivity for an alkali protease derived from a bacterium of the genus *Bacillus*, which protease comprising the amino acid sequence set forth in SEQ ID NO: 4, as an index. As control, evaluation was performed also for *Bacillus subtilis* strain 168, strain ΔsigF, strain ΔsigE and strain ΔphrA. That is, a DNA fragment (W) of 1.3 kb in size which encodes an alkali protease having the amino acid sequence set forth in SEQ ID NO: 3 (Appl. Microbiol. Biotechnol., 43, 473 (1995)), was amplified by performing PCR using the genome DNA extracted from *Bacillus clausii* strain KSM-K16 (FERM BP-3376) as a template, and using the primer set of S237pKAPpp-F and KAPter-R (BglII) shown in Table 1. Also, a DNA fragment (X) of 0.6 kb in size containing the promoter region of an alkali cellulase gene (JP-A No. 2000-210081), was amplified by performing PCR using the genome DNA extracted from Bacillus sp. strain KSM-S237 (FERM BP-7875) as a template, and using the primer set of S237 ppp-F2 (BamHI) and S237pKAPpp-R shown in Table 1. Subsequently, a DNA fragment (Y) of 1.8 kb in size, in which alkali protease gene is linked downstream to the promoter region of alkali cellulase gene, was obtained by performing SOE-PCR using a mixture of the obtained two fragments of (W) and (X) as a template, and using the primer set of S237 ppp-F2 (Bam HI) and KAPter-R (BglII) and the like shown in Table 1. The resulting DNA fragment (Y) of 1.8 kb was inserted at the BamHI-BglII restriction enzyme cleavage site of a shuttle vector, pHY300PLK (Yakult Honsha Co., Ltd.), to construct plasmid pHYKAP (S237p) for the evaluation of alkali protease production.

The constructed plasmid pHYKAP (S237p) was transfected into various bacterial strains according to the protoplast transformation method. Each of the obtained recombinant strains was subjected to shaking culture overnight at 37° C. in 10 mL of LB medium, and 0.05 mL of this culture solution was inoculated into 50 mL of 2×L-maltose medium (2% tryptone, 1% yeast extract, 1% NaCl, 7.5% maltose, 7.5 ppm manganese sulfate tetra- or pentahydrate, and 15 ppm tetracycline), and was subjected to shaking culture for 3 days at 30° C. After the culture, the supernatant of culture solution from which bacterial cells were removed by centrifugation, was measured for the alkali protease activity to determine the amount of the alkali protease secreted and produced outside the bacterial cells during the culture. The determination of the protease activity in the culture supernatant was performed as follows. Specifically, to 50 μL of the culture supernatant appropriately diluted with a 2 mM $CaCl_2$ solution, 100 μL of a 75 mM boric acid-KCl buffer solution (pH 10.5) containing 7.5 mM of Succinyl-L-Alanyl-L-Alanyl-L-Alanine p-Nitroanilide (STANA, Peptide Institute, Inc.) as a substrate, was added and mixed. Quantification of the amount of p-nitroaniline detached when a reaction was performed at 30° C., was carried out by measuring changes in the absorbance at 420 nm (OD420 nm). The amount of enzyme for detaching 1 μ-mol of p-nitroaniline in one minute was taken as 1 U.

As a result of the measurement of alkali protease activity, as shown in Table 3, when strain secY-K was used as the host, the productivity for alkali protease was equal to that of the control, strain 168 (wild type), and in particular, no improvement of productivity was recognized. On the other hand, significant improvement of productivity was observed with strain secYKΔsigF, strain secYKΔsigE and strain secYKΔphrA, in which deletions of sporulation-associated genes were combined. An improvement of productivity exceeding the improvement for strain 168 was also observed for strain ΔsigF, strain ΔsigE and strain ΔphrA, which were not subject to the introduction of enhancement in the expression of secY gene; however, the manifestation of the productivity improving effects resulting from deletion of these genes clearly was obviously increasing in the combination with the enhancement in the expression of secY gene. In other words, it was conceived that when the amount of SecY protein, which is the device for secretion, is first increased, and then deletion of the sporulation-associated genes such as sigF, sigE and phrA is provided, a synergistic effect is obtained in the improvement of productivity for heterologous proteins.

TABLE 3

| | Protease Activity (relative value, %) | Effect of deletion (%) |
| --- | --- | --- |
| 168 | 100 | — |
| ΔsigF | 219 | 119 |
| ΔsigE | 253 | 153 |
| ΔphrA | 154 | 54 |
| secY-K | 100 | — |
| SecYKΔsigF | 233 | 133 |
| SecYKΔsigE | 278 | 178 |
| SecYKΔphrA | 209 | 109 |

Example 5

Evaluation of Secretion and Production of Alkali Cellulase

An evaluation of productivity for other heterologous proteins was performed as follows, using the productivity for an alkali cellulase derived from a bacterium of the genus Bacillus, comprising the amino acid sequence set forth in SEQ ID NO: 6, as an index. Specifically, a fragment (3.1 kb) of alkali cellulase gene (JP-A No. 2000-210081) derived from Bacillus sp. strain KSM-S237 (FERM BP-7875) was amplified using the primer set of 237UB1 and 237 DB1 shown in Table 1, and then was treated with BamHI restriction enzyme to insert the fragment at the BamHI restriction enzyme cleavage site of shuttle vector pHY300PLK. Recombinant plasmid pHY-S237 thus obtained was transfected into various bacterial strains according to the protoplast transformation method. Each of the recombinant strains thus obtained was subjected to shaking culture for 3 days under the same conditions as in Example 4. The supernatant of culture solution from which bacterial cells were removed by centrifugation, was measured for the alkali cellulase activity to determine the amount of the alkali cellulase secreted and produced outside the bacterial cells during the culture.

For the determination of the cellulase activity, 50 μL of 0.4 mM p-nitrophenyl-β-D-cellotrioside (Seikagaku Corporation) was added to 50 μL of a sample solution appropriately diluted with a 1/7.5 M phosphate buffer solution (pH 7.4, Wako Pure Chemical Industries, Ltd.) and mixed, and quantification of the amount of p-nitrophenol detached when a reaction was performed at 30° C., was carried out by measuring changes in the absorbance at 420 nm (OD420 nm). The amount of enzyme for detaching 1 μmol of p-nitrophenol for one minute was taken as 1 U.

As a result of the measurement of alkali cellulase activity, as shown in Table 4, when strain secY-K was used as the host, higher secretion and production of alkali cellulase were recognized as compared to the case of the control, strain 168 (wild type). Also, further significant improvement of productivity was recognized with strain secYKΔsigF, strain secYKΔsigE and strain secYKΔphrA, in which deletions of sporulation-associated genes were combined. An improvement of productivity exceeding the improvement for strain 168 was also observed for strain ΔsigF, strain ΔsigE and strain ΔphrA, which were not subject to the introduction of enhancement in the expression of secY gene; however, the manifestation of the productivity improving effects resulting from deletion of these genes clearly was obviously increasing in the combination with the enhancement in the expression of secY gene. In other words, it was conceived that when the amount of SecY protein, which is the device for secretion, is first increased, and then deletion of the sporulation-associated genes such as sigF, sigE and phrA is provided, a synergistic effect is obtained in the improvement of productivity.

TABLE 4

| | Cellulase Activity (relative value, %) | Effect of deletion (%) |
|---|---|---|
| 168 | 100 | — |
| ΔsigF | 142 | 42 |
| ΔsigE | 145 | 45 |
| ΔphrA | 130 | 30 |
| secY-K | 115 | — |
| SecYKΔsigF | 162 | 62 |
| SecYKΔsigE | 167 | 67 |
| SecYKΔphrA | 155 | 55 |

Comparative Example 1

Substitution of rsiX Gene with Drug Resistance Gene

Substitution of rsiX gene on the genome of *Bacillus subtilis* strain 168 with a chloramphenicol resistance gene was performed in the same manner as in the substitution of sigF gene with a spectinomycin resistance gene shown in Example 2, to construct strain ΔrsiX. The primers used are shown in Table 1, and the correspondence of the respective primers to the primers used in the construction of strain ΔsigF is shown in Table 2. Strain ΔsigFΔrsiX was also constructed by substituting rsiX gene on the genome of the strain ΔsigF constructed in Example 2, with a chloramphenicol resistance gene in the same manner. Additionally, the rsiX gene is a gene encoding an anti-sigma factor (anti-SigX) that suppresses the function of SigX, which is one of sigma factors belonging to ECF (extracytoplasmic function) family of *Bacillus subtilis*. SigX is activated when the environment around the cells changes under thermal stress or the like, and has a function of coping with the environmental change by inducing the transcription of a gene having a promoter for recognizing the activation, or of an operon (J. Bacteriol., 179, 2915 (1997)).

Comparative Example 2

Evaluation of Secretion and Production of Alkali Protease

Evaluation of secretion productivity for alkali protease of the strain ΔsigFΔrsiX constructed in Comparative Example 1 was performed in the same manner as in Example 4. As a control, the same evaluation was performed for *Bacillus subtilis* strain 168, strain ΔrsiX and the strain ΔsigF constructed in Example 1.

As a result, as shown in Table 5, although the productivity for protease of the strain ΔrsiX with deleted rsiX gene was higher than that of the wild type strain 168, the productivity of strain ΔsigFΔrsiX in which deletion of sigF gene was combined was rather lower than that of strain ΔsigF. In other words, it was confirmed that manifestation of a synergistic effect for the production of heterologous proteins when deletions of sporulation-associated gene are combined, is not recognized for the deletion of rsiX gene.

TABLE 5

| | Protease Activity (relative value, %) |
|---|---|
| 168 | 100 |
| ΔsigF | 188 |
| ΔrsiX | 123 |
| ΔrsiXΔsigF | 178 |

Comparative Example 3

Substitution of yacP Gene, yvdE Gene, yurK Gene, yhdQ Gene and glcT Gene with Drug Resistance Gene Substitution of yacP gene, yvdE gene, yurK gene, yhdQ gene and glcT gene on the genome of *Bacillus subtilis* strain 168 with a chloramphenicol resistance gene performed in the same manner as in the substitution of sigF gene with a spectinomycin resistance gene shown in Example 2, to construct strain ΔyacP, strain ΔyvdE, strain ΔyurK, strain ΔyhdQ and strain ΔglcT, respectively. The primers used are shown in Table 1, and the correspondence of the respective primers used to the primers used in the construction of strain ΔsigF is shown in Table 2. Also, by substituting yacP gene, yvdE gene, yurK gene, yhdQ gene and glcT gene on the genome of strain ΔsigF constructed in Example 2, with a chloramphenicol resistance gene, strain ΔsigFΔyacP, strain ΔsigFΔyvdE, strain ΔsigFΔyurK, strain ΔsigFΔyhdQ and strain ΔsigFΔglcT were respectively constructed.

With regard to the genes related to the present invention, the gene No. and function thereof are presented in Table 6.

TABLE 6

| Name of Gene | Gene No. | Function |
|---|---|---|
| secY | BG10445 | Preprotein translocase SecY subunit |
| spoVG | BG10112 | Stage V sporulation protein G (Synthesis of spore cortex) |
| amyE | BG10473 | α-Amylase |
| sigA | BG10314 | RNA polymerase main sigma factor |
| kinA | BG10204 | Two-component regulatory sensor histidine kinase A involved in the initiation of sporulation |
| kinB | BG10745 | Two-component regulatory sensor histidine kinase B involved in the initiation of sporulation |
| kinC | BG10989 | Two-component regulatory sensor histidine kinase C involved in the initiation of sporulation |
| spo0F | BG10411 | Two-component regulatory response regulator involved in the initiation of sporulation |
| spo0B | BG10336 | Sporulation initiating phosphotransferase |
| spo0A | BG10765 | Two-component regulator response regulator leading the initiation of sporulation |
| kapB | BG10746 | Activation of KinB in the initiation of sporulation |
| kipI | BG11231 | Inhibition of the function of KinA |
| kipA | BG11214 | Control factor for the transcription of kip operon |

TABLE 6-continued

| Name of Gene | Gene No. | Function |
|---|---|---|
| rapA | BG10652 | Aspartate phosphatase A inhibiting the phosphate relay system by dephosphorylation of phosphorylated Spo0F |
| phrA | BG10653 | Inhibitory factor for the activity of aspartate phosphatase A (RapA) |
| soj | BG10055 | Soj protein involved in the inhibition of cell cycle and initiation of replication |
| spo0J | BG10054 | Stage 0 sporulation protein J. Inhibition of the function of Soj |
| sigH | BG10159 | RNA polymerase sigma H factor for the log phase and the early stage of stationary phase |
| sigF | BG10298 | RNA polymerase sporulation-specific sigma F factor |
| sigE | BG10235 | RNA polymerase sporulation-specific sigma E factor |
| spoIIAA | BG10296 | Anti-anti-sigma factor (antagonist of SpoIIAB) |
| spoIIAB | BG10297 | Anti-sigma factor (inhibition of sigma F) |
| spoIIE | BG10127 | PP2C serine phosphatase involved in the formation of asymmetric septum (activation of sigma F) |
| spoIIR | BG10937 | Stage II sporulation protein R (activation of SpoIIGA) |
| spoIIGA | BG10234 | Protease involved in the generation of active sigma E through processing of Prosigma E |
| sigG | BG10236 | RNA polymerase sporulation-specific sigma G factor |
| spoIIIC | BG10919 | RNA polymerase sporulation-specific sigma K factor (C-terminal side) |
| spoIVCB | BG10459 | RNA polymerase sporulation-specific sigma K factor (N-terminal side) |
| rsiX | BG10537 | Anti-sigma X protein (inhibition of sigma X factor) |
| yacP | BG10158 | Gene with unknown function |
| yvdE | BG12414 | Suspected transcription factor (LacI family) |
| yurK | BG13997 | Suspected transcription factor (GntR family) |
| yhdQ | BG13023 | Factor for activating the transcription of copper ion transport system operon (copZA) |
| glcT | BG12593 | Transcription antiterminator essential for the expression of ptsGHI operon |

Comparative Example 4

Evaluation of Secretion and Production of Alkali Cellulase

Evaluation of the secretion productivity for alkali cellulase of the strain ΔyacP, strain ΔyvdE, strain ΔyurK, strain ΔyhdQ and strain ΔglcT constructed in Comparative Example 3 was performed in the same manner as in Example 5. As a control, evaluation was performed also for Bacillus subtilis strain 168. As a result, as shown in Table 7, the a productivity higher than that of the wild type strain was recognized with strain ΔyacP, strain ΔyvdE, strain ΔyurK, and strain ΔglcT, while the productivity was slightly decreased with strain ΔyhdQ. Furthermore, evaluation of the secretion productivity for alkali cellulase of the strain ΔsigFΔyacP, strain ΔsigFΔyvdE, strain ΔsigFΔyurK, strain ΔsigFΔyhdQ and strain ΔsigFΔglcT constructed in Comparative Example 3 was performed in the same manner as in Example 5. As a control, the evaluation was also performed for Bacillus subtilis strain 168 and the strain ΔsigF constructed in Example 1. As a result, as shown in Table 8, with any of the constructed strains, the productivity for cellulase was lower than that of strain ΔsigF. In other words, it was strongly suggested that manifestation of a synergistic effect for the production of heterologous proteins when deletions of sporulation-associated genes are combined, is a feature for the combination with enhancement of the expression of secY gene.

TABLE 7

| | Cellulase Activity (relative value, %) |
|---|---|
| 168 | 100 |
| ΔyacP | 156 |
| ΔyvdE | 109 |
| ΔyurK | 118 |
| ΔyhdQ | 97 |
| ΔglcT | 110 |

TABLE 8

| | Cellulase Activity (relative value, %) |
|---|---|
| 168 | 100 |
| ΔsigF | 161 |
| ΔsigFΔyacP | 154 |
| ΔsigFΔyvdE | 147 |
| ΔsigFΔyurk | 158 |
| ΔsigFΔyhdQ | 154 |
| ΔsigFΔglcT | 151 |

The invention claimed is:

1. A recombinant *Bacillus subtilis* host cell comprising
    (a) a transfected gene encoding a desired protein or polypeptide,
    (b) a genetic modification to overexpress a secY gene of a *Bacillus* species in said recombinant *Bacillus subtilis* host cell as compared to expression of said secY gene in a *Bacillus subtilis* host cell that is the same except that it lacks said genetic modification of said secY gene, and
    (c) deletion, from the genome of said recombinant *Bacillus subtilis* host cell, of one or more sporulation-associated genes selected from the group consisting of the kinA gene, kinB gene, kinC gene, spo0F gene, spo0B gene, spo0A gene, kapB gene, kipA gene, phrA gene, spo0J gene, sigH gene, sigF gene, sigE gene, spoIIAA gene, spoIIAB gene, spoIIE gene, spoIIR gene, spoIIGA gene, sigG gene, spoIIIC gene, and spoIVCB gene, wherein secretion of said desired protein or polypeptide from said recombinant host cell is greater than the secretion achieved by either overexpression of said secY gene or deletion of said one or more sporulation-associated genes alone,
    wherein said secY gene is the only gene associated with the Sec route of *B. subtilis* that is overexpressed in said host cell, and
    wherein said genetic modification to overexpress said secY gene comprises introduction of:
        (i) a transcription initiation control region, or a transcription initiation control region and a ribosome binding site, that function in said host cell, upstream of said *Bacillus* species secY gene, or
        (ii) a transcription initiation control region, or a transcription initiation control region and a ribosome binding site, that function in said host cell, upstream of the leader gene of an operon containing said *Bacillus* species secY gene, or
        (iii) a gene fragment in which a transcription initiation control region, or a transcription initiation control region and a ribosome binding site, that function in said host cell, are linked upstream of said *Bacillus* species secY gene,
            wherein said transcription initiation control region or said transcription initiation control region and ribosome binding site of parts (i), (ii) and (iii) are from a *B. subtilis* spoVG gene or a *B. subtilis* aprE gene.

2. The recombinant *Bacillus subtilis* host cell according to claim 1, wherein the sporulation-associated genes are one or more genes selected from the group consisting of said sigF gene, sigE gene, and phrA gene.

3. The recombinant *Bacillus subtilis* host cell according to claim 1, wherein, in addition to said transcription initiation control region as recited in claim 1, said host cell further comprises any one or more regions selected from the group consisting of a translation initiation control region and a secretion signal region ligated upstream of the gene encoding said desired protein or polypeptide.

4. The recombinant *Bacillus subtilis* host cell according to claim 3, wherein said recombinant host cell comprises both said translation initiation control region and said secretion signal.

5. The recombinant *Bacillus subtilis* host cell according to claim 3, wherein said transcription initiation control region, said translation initiation control region and said secretion signal region are from a cellulase gene of a bacterium of the genus *Bacillus*, and said transcription initiation control region and said translation initiation control region are from regions of 0.6 to 1 kb in size upstream of said cellulase gene.

6. The recombinant *Bacillus subtilis* host cell according to claim 3, wherein the transcription initiation control region, translation initiation control region and secretion signal region, form a DNA fragment comprising:
    a) a nucleic acid sequence from base No. 1 to base No. 659 of a cellulase gene having the nucleic acid sequence set forth in SEQ ID NO: 5,
    b) a nucleic acid sequence from base No. 1 to base No. 696 of a cellulase gene having the nucleic acid sequence set forth in SEQ ID NO: 7,
    c) a base sequence having at least 95% identity to the nucleic acid sequences of a) or b).

7. A method of producing the recombinant *Bacillus subtilis* host cell as set forth in claim 1, which comprises,
    introducing into a *Bacillus subtilis* host cell
    a transcription initiation control region or a transcription initiation control region and a ribosome binding site, that function in said microorganism, upstream of a *Bacillus* species secY gene, or upstream of the leader gene of an operon containing a *Bacillus* species secY gene, or introducing a gene fragment in which a transcription initiation control region or a transcription initiation control region and a ribosome binding site, that function in said microorganism, is linked upstream of a *Bacillus* species secY gene
    to produce a genetic modification that results in overexpression of said secY gene in said recombinant *Bacillus subtilis* host cell as compared to expression of said secY gene in a *Bacillus subtilis* host cell that is the same except that it lacks said genetic modification of said secY gene;
    deleting or inactivating one or more sporulation-associated genes; and
    transfecting a gene encoding a desired protein or polypeptide into said host cell.

8. A method for producing a desired protein or polypeptide comprising:
    i. culturing the recombinant *Bacillus subtilis* host cell according to claim 1 in which said secY gene is overexpressed in a culture medium under conditions that permit the expression of the transfected gene encoding a desired protein or polypeptide; and ii. collecting the desired protein or polypeptide from the culture medium.

9. The recombinant *Bacillus subtilis* host cell according to claim 6, wherein the transcription initiation control region, translation initiation control region and secretion signal region, form a DNA fragment comprising said nucleic acid sequence from base No. 1 to base No. 659 of a cellulase gene having the nucleic acid sequence set forth in SEQ ID NO: 5.

10. The recombinant *Bacillus subtilis* host cell according to claim 6, wherein the transcription initiation control region, translation initiation control region and secretion signal region, form a DNA fragment comprising said nucleic acid sequence from base No. 1 to base No. 696 of a cellulase gene having the nucleic acid sequence set forth in SEQ ID NO: 7.

11. A recombinant *Bacillus subtilis* host cell comprising genetic modifications, wherein said genetic modifications consist essentially of:
(a) a transfected gene encoding a desired protein or polypeptide,
(b) a genetic modification to overexpress a secY gene of a *Bacillus* species in said recombinant host cell as compared to expression of said secY gene in a *Bacillus subtilis* host cell that is the same except that it lacks said genetic modification of said secY gene, wherein said secY gene is the only gene associated with the Sec route of *B. subtilis* that is overexpressed in said host cell, and
(c) deletion, from the genome of said recombinant *Bacillus subtilis* host cell, of one or more sporulation-associated genes selected from the group consisting of the kinA gene, kinB gene, kinC gene, spo0F gene, spo0B gene, spo0A gene, kapB gene, kipA gene, phrA gene, spo0J gene, sigH gene, sigF gene, sigE gene, spoIIAA gene, spoIIAB gene, spoIIE gene, spoIIR gene, spoIIGA gene, sigG gene, spoIIIC gene, and spoIVCB gene, wherein secretion of said desired protein or polypeptide from said recombinant *Bacillus subtilis* host cell is greater than the secretion achieved by either overexpression of said secY gene or deletion of said sporulation-associated gene alone, and
wherein said genetic modification to overexpress said secY gene comprises introduction of:
(i) a transcription initiation control region, or a transcription initiation control region and a ribosome binding site, that function in said host cell, upstream of said *Bacillus* species secY gene, or
(ii) a transcription initiation control region, or a transcription initiation control region and a ribosome binding site, that function in said host cell, upstream of the leader gene of an operon containing a *Bacillus* species secY gene, or
(iii) a gene fragment in which a transcription initiation control region, or a transcription initiation control region and a ribosome binding site, that function in said host cell, are linked upstream of a *Bacillus* species secY gene,
wherein said transcription initiation control region or said transcription initiation control region and ribosome binding site of parts (i), (ii) and (iii) are from a *B. subtilis* spoVG gene or a *B. subtilis* aprE gene.

* * * * *